US009725752B2

(12) United States Patent
Johnson et al.

(10) Patent No.: US 9,725,752 B2
(45) Date of Patent: Aug. 8, 2017

(54) RESONATOR AND PROCESS FOR PERFORMING BIOLOGICAL ASSAY

(71) Applicant: THE UNITED STATES OF AMERICA, AS REPRESENTED BY THE SECRETARY OF COMMERCE, Washington, DC (US)

(72) Inventors: Ward L. Johnson, Louisville, CO (US); Danielle C. France, Golden, CO (US); Teresa L. Kirschling, Golden, CO (US); Fred L. Walls, Layayette, CO (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/236,943

(22) Filed: Aug. 15, 2016

(65) Prior Publication Data
US 2017/0044589 A1    Feb. 16, 2017

Related U.S. Application Data

(60) Provisional application No. 62/204,645, filed on Aug. 13, 2015.

(51) Int. Cl.
*C12M 1/34*     (2006.01)
*C12Q 1/18*     (2006.01)
(Continued)

(52) U.S. Cl.
CPC ............... *C12Q 1/18* (2013.01); *B01L 3/502* (2013.01); *G01N 29/2437* (2013.01);
(Continued)

(58) Field of Classification Search
CPC ............... C12Q 1/18; G01N 29/2437; G01N 2291/0255; G01N 2333/245;
(Continued)

(56) References Cited

U.S. PATENT DOCUMENTS

| 4,554,717 A | 11/1985 | Vig et al. |
| 5,135,852 A * | 8/1992 | Ebersole ............... C12Q 1/04 435/34 |
| 7,802,466 B2 * | 9/2010 | Whalen ............ B01L 3/502776 73/54.41 |

OTHER PUBLICATIONS

Baer et al., "Phase Noise Measurements of Flexuarl Plate Wave Ultrasonic Sensors", IEEE Ultrasonics Symposium (1991), pp. 321-326.*

(Continued)

*Primary Examiner* — William H Beisner
(74) *Attorney, Agent, or Firm* — Toby D. Hain

(57) ABSTRACT

A process for assaying a biological sample includes: receiving a reference sample by an acoustic article including: a resonator including: a substrate; a piezoelectric member; and a phase noise detector; disposing the reference sample on the piezoelectric member; producing a reference phase noise signal; detecting the reference phase noise signal; disposing a biological sample on the piezoelectric member; producing a first biological phase noise signal; detecting the first biological phase noise signal; contacting the biological sample disposed on the piezoelectric member with an antimicrobial agent; producing a second biological phase noise signal; detecting the second biological phase noise signal; and analyzing the first biological phase noise signal, the second biological phase noise signal, and the reference phase noise signal to assay the biological sample.

16 Claims, 37 Drawing Sheets

(51) Int. Cl.
*B01L 3/00* (2006.01)
*G01N 29/24* (2006.01)

(52) U.S. Cl.
CPC .......... B01L 2200/0647 (2013.01); *B01L 2300/0645* (2013.01); *B01L 2300/0861* (2013.01); *G01N 2291/0255* (2013.01); *G01N 2333/245* (2013.01)

(58) Field of Classification Search
CPC ....... B01L 2200/647; B01L 2300/0645; B01L 2300/0861; H03H 9/13; H03H 9/17
See application file for complete search history.

(56) References Cited

OTHER PUBLICATIONS

G. Longo et al., "Rapid detection of bacterial resistance to antibiotics using AFM cantilevers as nanomechanical sensors," Nature Nanotechnology, 2013, 522-526, vol. 8.

S. Winters et al., "Lateral Field Excitation of Well Structures in Quartz," Proceedings of the 2008 IEEE Ultrasonics Symposium, 2008, 272-275.

J. Rabe et al., "Monolithic Miniaturized Quartz Microbalance Array and Its Application to Chemical Sensor Systems for Liquids," IEEE Sensors Journal, 2003, 361-368, vol. 3.

J. Liang et al., "Flow-Injection-Based Miniaturized Quartz Crystal Microbalance," Sensors and Materials, 2013, 519-526, vol. 25.

A. Sapper et al., "Cell Motility Probed by Noise Analysis of Thickness Shear Mode Resonators," Anal. Chem., 2006, 5184-5191, vol. 78.

A. Sapper, Mechanics and Dynamics of Liposomes and Cells Studied by QCM and ECIS, PhD thesis, Johannes Gutenberg University, Mainz, Germany, 2006.

C. Lissandrello et al., "Nanomechanical motion of *Escherichia coli* adhered to a surface", Applied Physics Letters, 2014, 113701-1-113701-5, vol. 5.

K. Syal et al., "Antimicrobial Susceptibility Test with Plasmonic Imaging and Tracking of Single Bacterial Motions on Nanometer Scale", ACS Nano, 2015, A-H.

A. Tuantranont et al., "A review of monolithic multichannel quartz crystal microbalance: A review", Analytica Chimica Acta, 2011, 114-128, vol. 687.

K. Lakin, "Thin Film Resonator Technology", IEEE Trans UFFC, 2005, 707-716, vol. 52, No. 5.

J. Gao et al., "Recent developments of film bulk acoustic resonators", Functional Material Letters, 2016, 1630002-1-1630002-10, vol. 9, No. 3.

F. Walls et al., "Measurement of the Short-Term Stability of Quartz Crystal Resonators and the Implications for Crystal Oscillator Design and Applications", IEEE Transaction on Instrumentation and Measurement, 1975, 15-20, vol. IM-24, No. 1.

* cited by examiner a) 101 b) 101 a) 101 b) 101 a) 101 b) 101 a) 101 b) 101 a) 101 b) 101 a) 101 b) 101 a) 101 b) 101 a) 101 b) 101 a) 101 b) 101 a) 101 b) 101 a) 101 b) 101 a) <u>101</u> b) <u>101</u> a) 100 b) 101 a) 101 b) 101

RESONATOR AND PROCESS FOR PERFORMING BIOLOGICAL ASSAY

CROSS REFERENCE TO RELATED APPLICATIONS

This application claims the benefit of U.S. Provisional Patent Application Ser. No. 62/204,645, filed Aug. 13, 2015, the disclosure of which is incorporated herein by reference in its entirety.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is an acoustic article for assaying a biological sample, the article comprising: a resonator comprising: a substrate; a piezoelectric member disposed on the substrate to receive the biological sample and to produce a phase noise signal, the phase noise signal indicating activity of the biological sample; and a phase noise detector in electrical communication with the piezoelectric member to receive the phase noise signal from the piezoelectric member and to produce a phase noise spectrum in response to receiving the phase noise signal from the piezoelectric member.

Also disclosed is a process for assaying a biological sample, the process comprising: receiving a reference sample by an acoustic article, the acoustic article comprising: a resonator comprising: a substrate; a piezoelectric member disposed on the substrate; and a phase noise detector; disposing the reference sample on the piezoelectric member; producing a reference phase noise signal in response to the piezoelectric member being in contact with the reference sample; detecting the reference phase noise signal by the phase noise detector; disposing a biological sample on the piezoelectric member, the biological sample comprising a microbe having a motional fluctuation on the piezoelectric member; producing a first biological phase noise signal in response to the piezoelectric member being in contact with the biological sample; detecting the first biological phase noise signal by the phase noise detector; contacting the biological sample disposed on the piezoelectric member with an antimicrobial agent; producing a second biological phase noise signal in response to the piezoelectric member being in contact with the biological sample; detecting the second biological phase noise signal by the phase noise detector; and analyzing the first biological phase noise signal, the second biological phase noise signal, and the reference phase noise signal to assay the biological sample.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that an acoustic article and process herein provides characterization of mechanical fluctuations of biological analytes (e.g., cells) in a fluid through acquisition of phase noise from a piezoelectric member. Advantageously and unexpectedly, the acoustic article provides determination of an effect of an antimicrobial agent on activity of microbes. It is contemplated that the acoustic article and process provide a rapid and efficient assay for an antimicrobial response of microbes involved in pathogenic infections in clinical settings.

Figure 1:
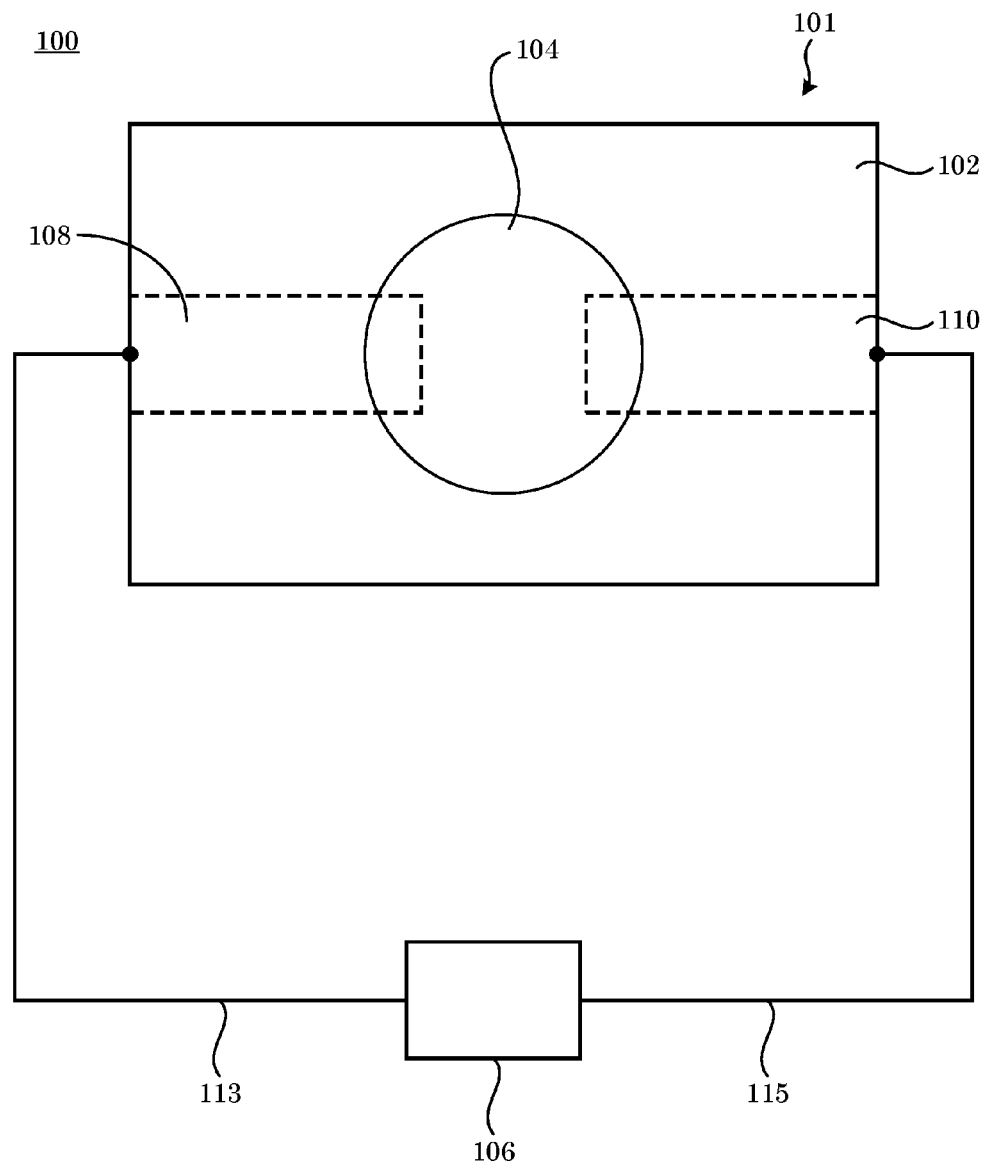
FIG. 1 shows an acoustic article.

In an embodiment, with reference to FIG. 1, acoustic article 100 includes resonator 101 that includes substrate 102, piezoelectric member 104 disposed on substrate 102, and phase noise detector 106 in electrical communication with piezoelectric member 104 via electrodes 108, 110. Communication paths (113, 115) electrically interconnect phase noise detector 106 to electrodes (108, 110). Here, piezoelectric member 104 receives a biological sample (not shown) and produces a phase noise signal. The phase noise signal indicates activity of the biological sample. Also, phase noise detector 106 receives the phase noise signal from piezoelectric member 104 and produces a phase noise spectrum in response to receiving the phase noise signal from piezoelectric member 104. Electrodes (108, 110) provide excitation of vibration of piezoelectric member 104 via an applied potential difference thereto.

Resonator 101 includes piezoelectric member 104 disposed on substrate 102 and can be a monolithic structure or separate components arranged in a composite format. Resonator 101 can have an inverted mesa structure provided by a difference in thickness of piezoelectric member 104 and substrate 102.

Figure 2:
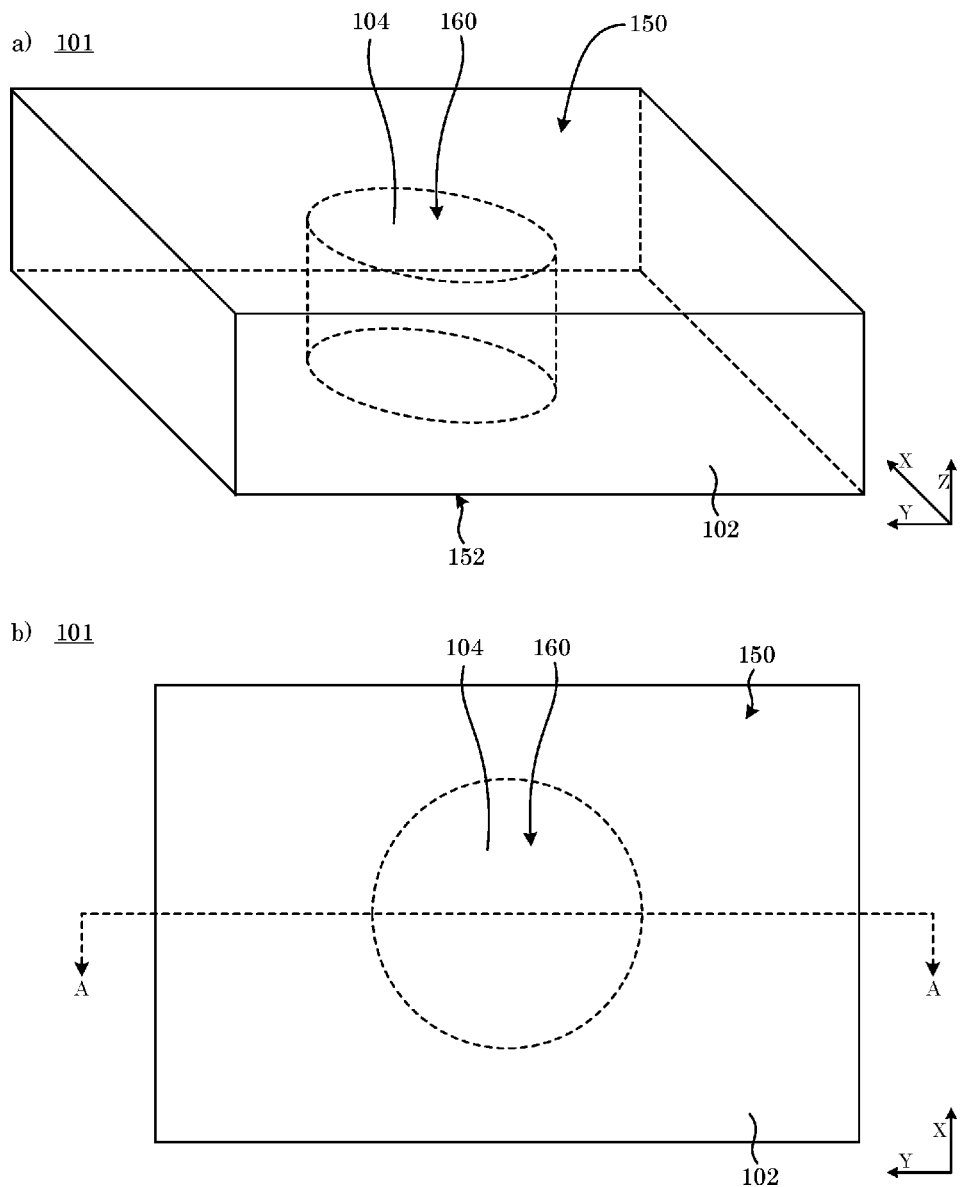
FIG. 2 shows a resonator.
Figure 3:
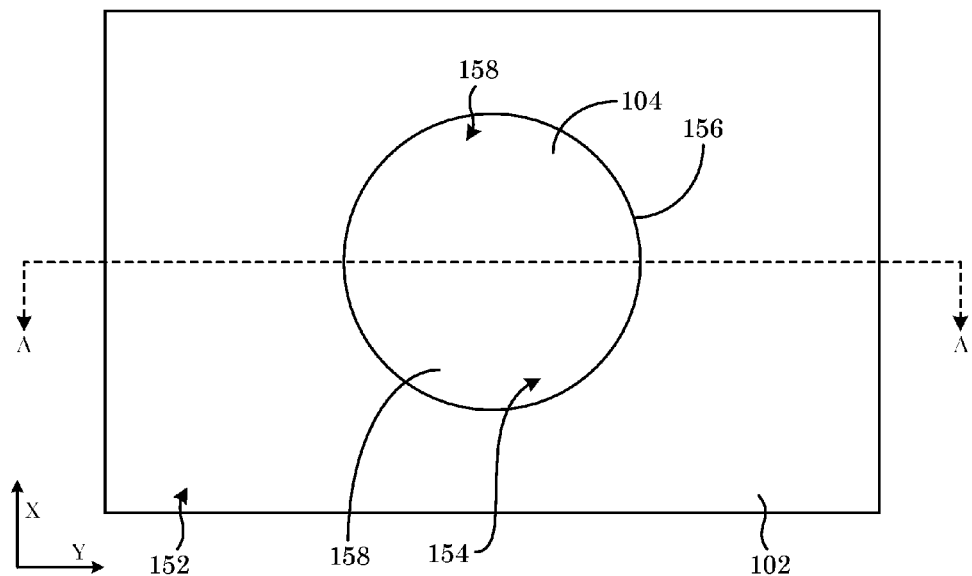
FIG. 3 shows a resonator.
Figure 3:
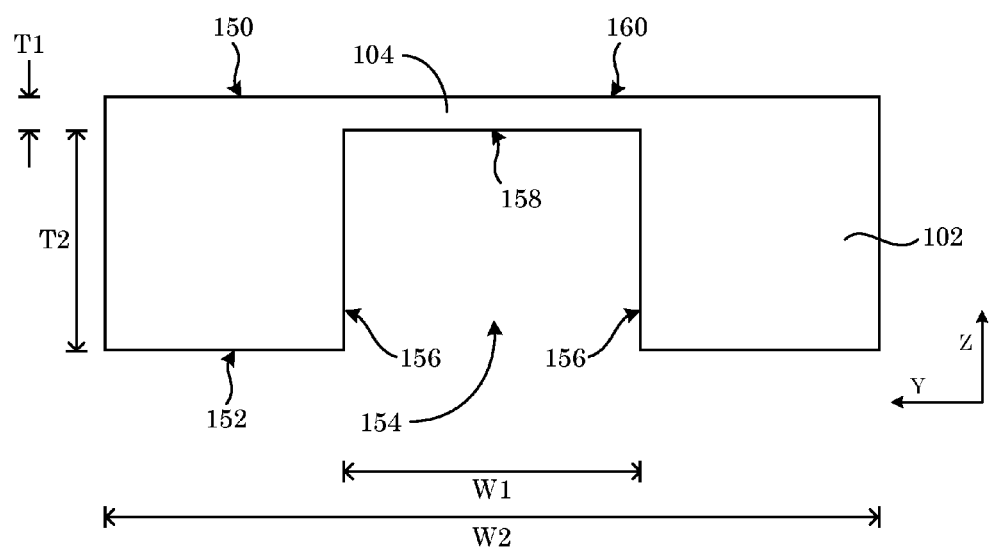

In an embodiment, with reference to FIG. 2 (panel a: perspective view; panel b: top view) and FIG. 3 (panel a: bottom view; panel b: cross-section along line A-A shown in FIG. 2), resonator 101 includes a single crystal inverted mesa resonator. Here, piezoelectric member 104 is integrally disposed as part of substrate 102, wherein piezoelectric member 104 is present at first surface 150 that opposes second surface 152 of substrate 102. Accordingly, piezoelectric member 104 and substrate 102 can be made of the same material, e.g., single crystal quartz. In some embodiments, piezoelectric member 104 and substrate 102 include different materials. Additionally, resonator 101 includes inverted mesa 154 bounded by wall 156 of substrate 102 and mesa surface 158 of piezoelectric member 104. Mesa surface 158 opposes basal surface 160 of piezoelectric member 104. Moreover, resonator 101 has width W1 and second width W2. Piezoelectric member 104 has first thickness T1, and substrate 102 has second thickness T2.

Figure 4:
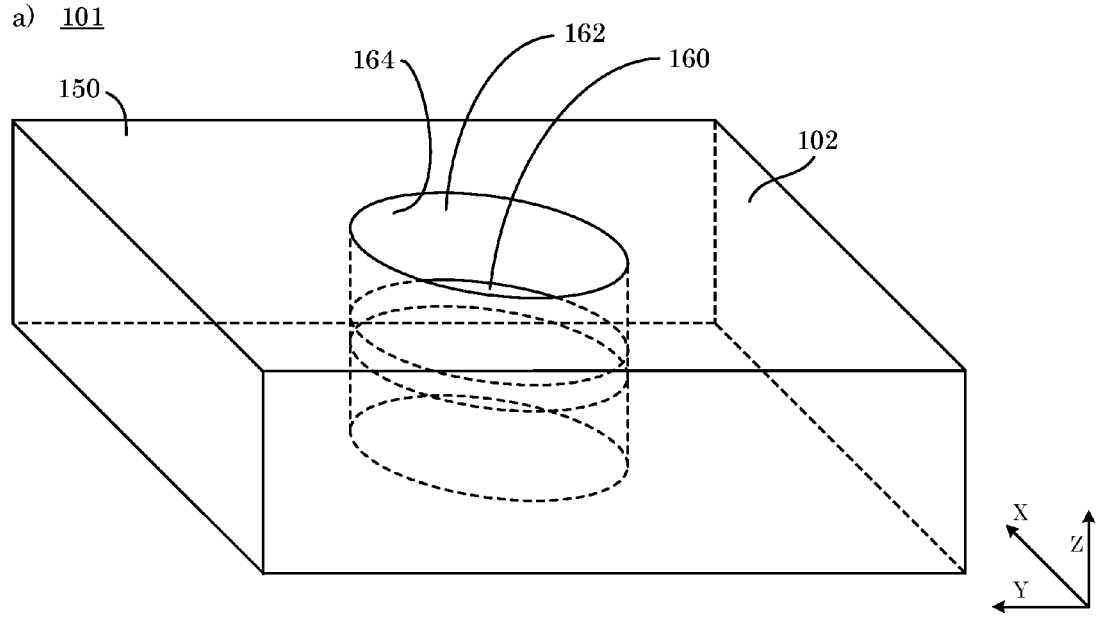
FIG. 4 shows a resonator.
Figure 4:
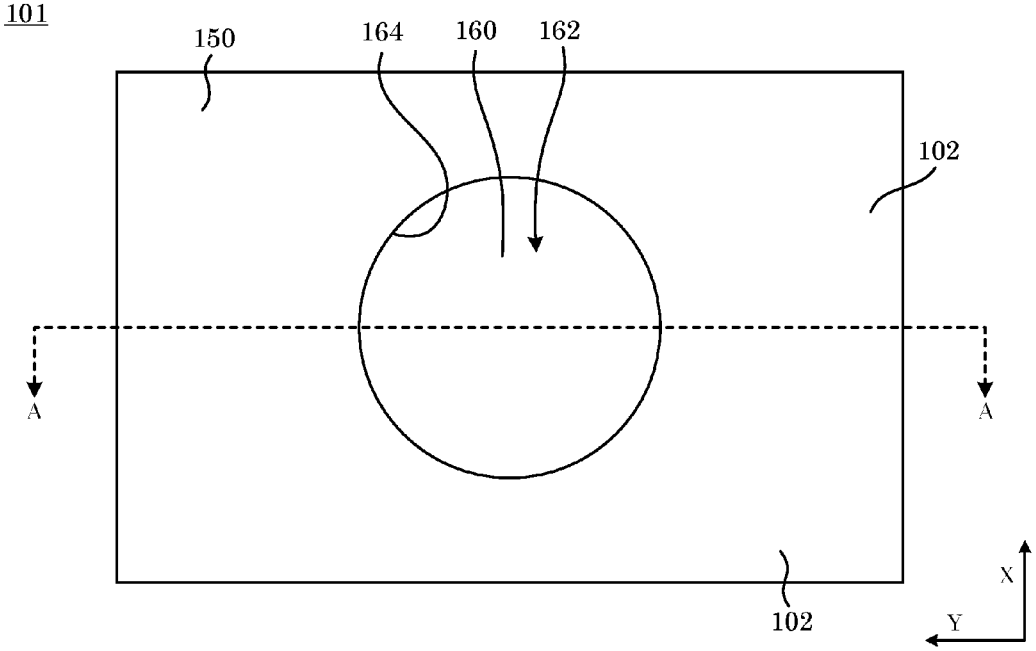
Figure 5:
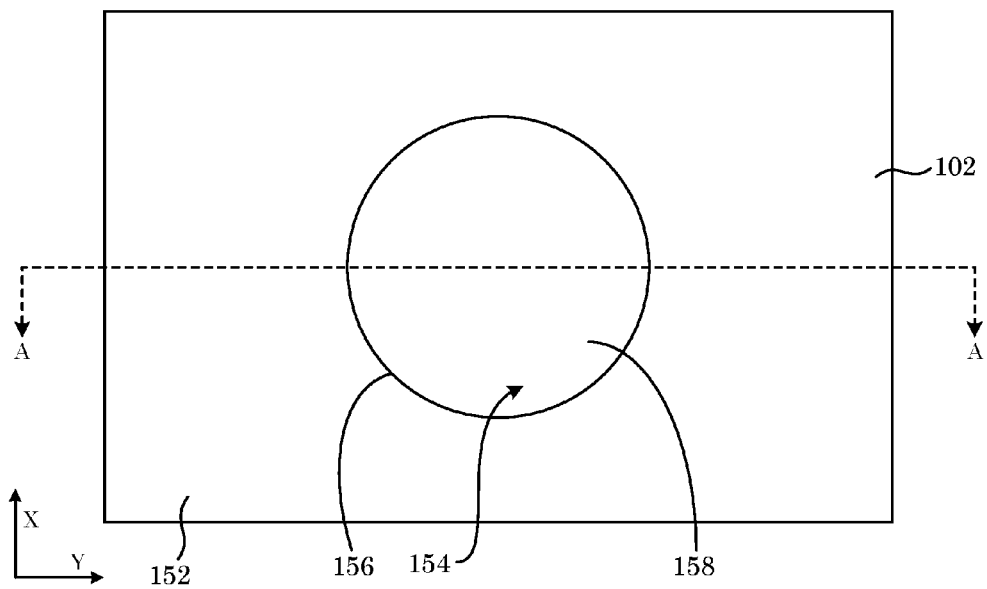
FIG. 5 shows a resonator.
Figure 5:
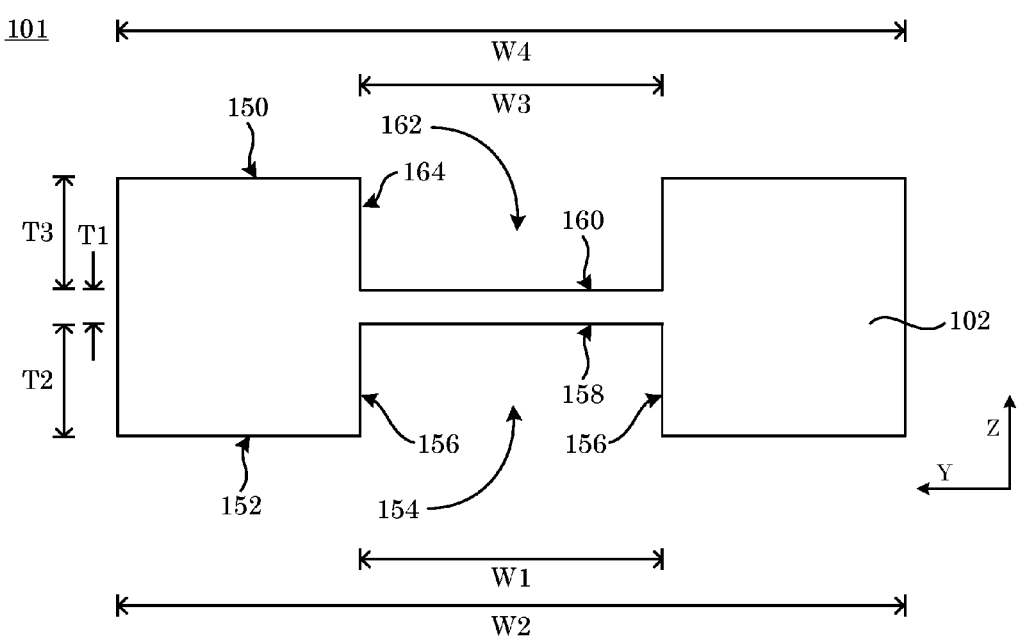

In an embodiment, with reference to FIG. 4 (panel a: perspective view; panel b: top view) and FIG. 5 (panel a: bottom view; panel b: cross-section along line A-A shown in FIG. 4), resonator 101 includes a single crystal inverted mesa resonator. Here, piezoelectric member 104 is integrally disposed as part of substrate 102, wherein piezoelectric member 104 is disposed intermediately between first surface 150 and second surface 152 of substrate 102. Here, resonator 101 also includes second inverted mesa 162 bounded by wall 164 of substrate 102 and basal surface 160 of piezoelectric member 104. Moreover, second inverted mesa 162 has width W3 a thickness T3 such that a portion of resonator 101 that includes second inverted mesa 162 has width W4.

Figure 6:
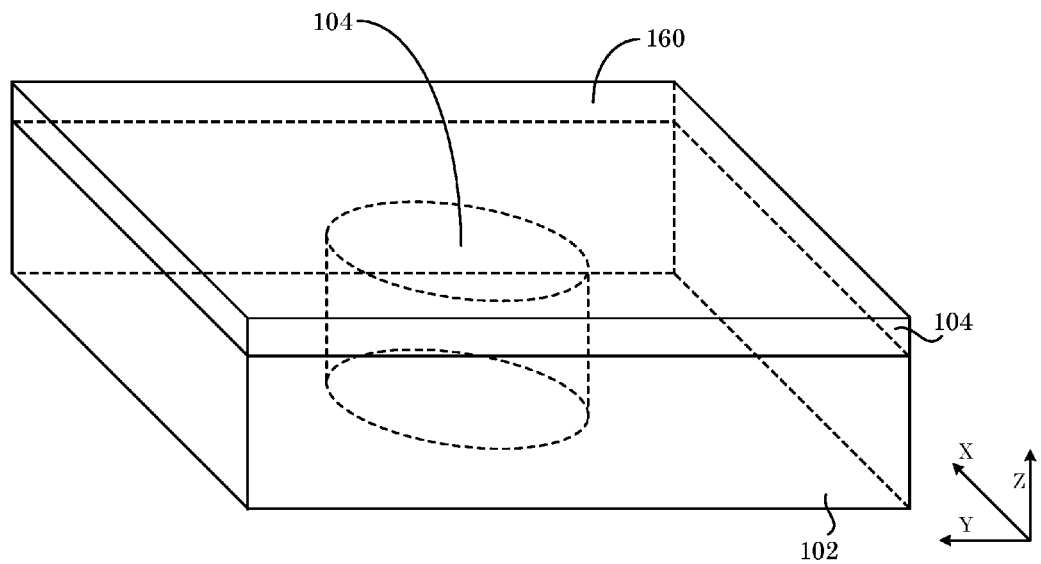
FIG. 6 shows a resonator.
Figure 6:
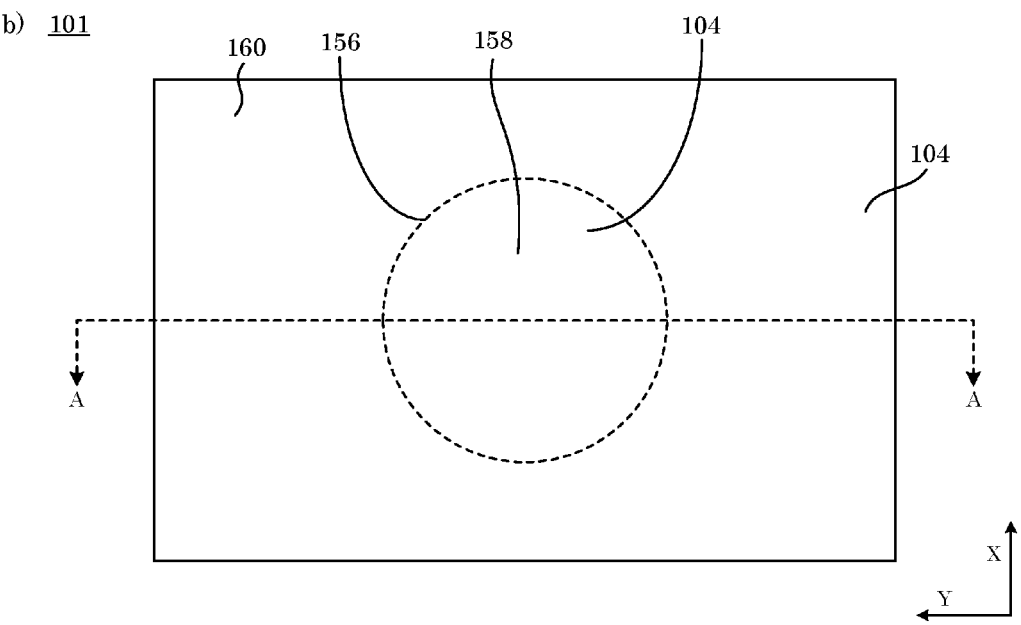
Figure 7:
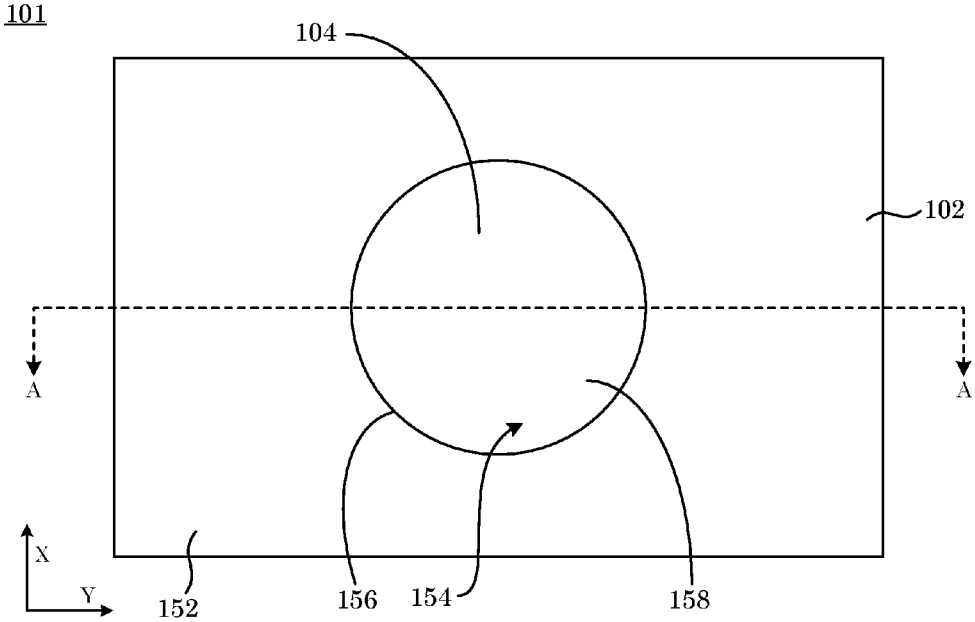
FIG. 7 shows a resonator.
Figure 7:
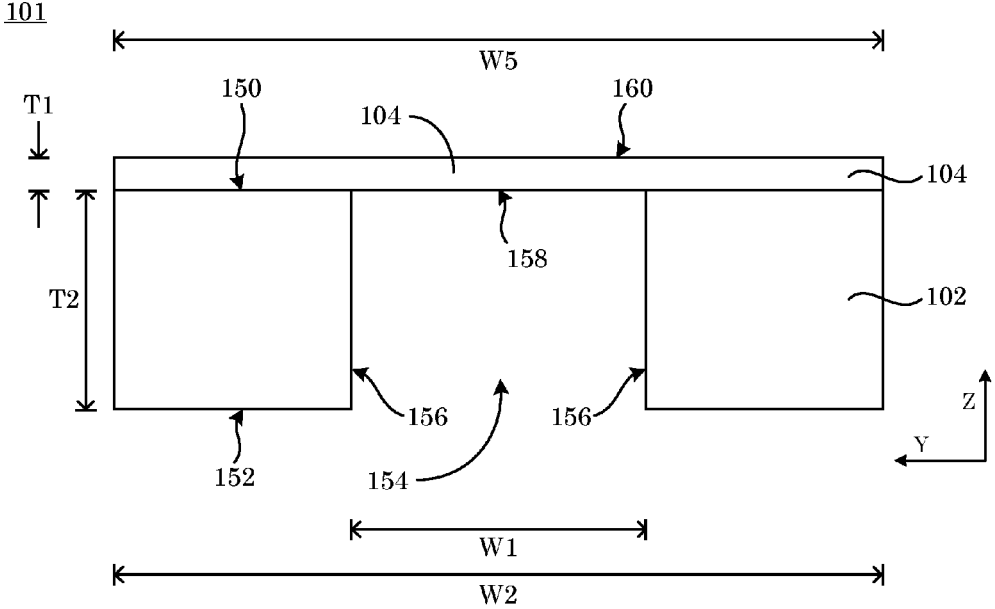

In an embodiment, with reference to FIG. 6 (panel a: perspective view; panel b: top view) and FIG. 7 (panel a: bottom view; panel b: cross-section along line A-A shown in FIG. 6), resonator 101 includes a film bulk acoustic resonator. Here, piezoelectric member 104 is stackedly disposed on substrate 102, wherein piezoelectric member 104 is present at first surface 150 that opposes second surface 152 of substrate 102. Accordingly, piezoelectric member 104 and substrate 102 can include different or same materials. Additionally, resonator 101 includes inverted mesa 154 bounded by wall 156 of substrate 102 and mesa surface 158 of piezoelectric member 104. Mesa surface 158 opposes basal surface 160 of piezoelectric member 104. Moreover, inverted message 154 has first width W1, and substrate 101 has second width W2 and thickness T2. Piezoelectric member 104 has first thickness T1 and width T5.

Figure 8:
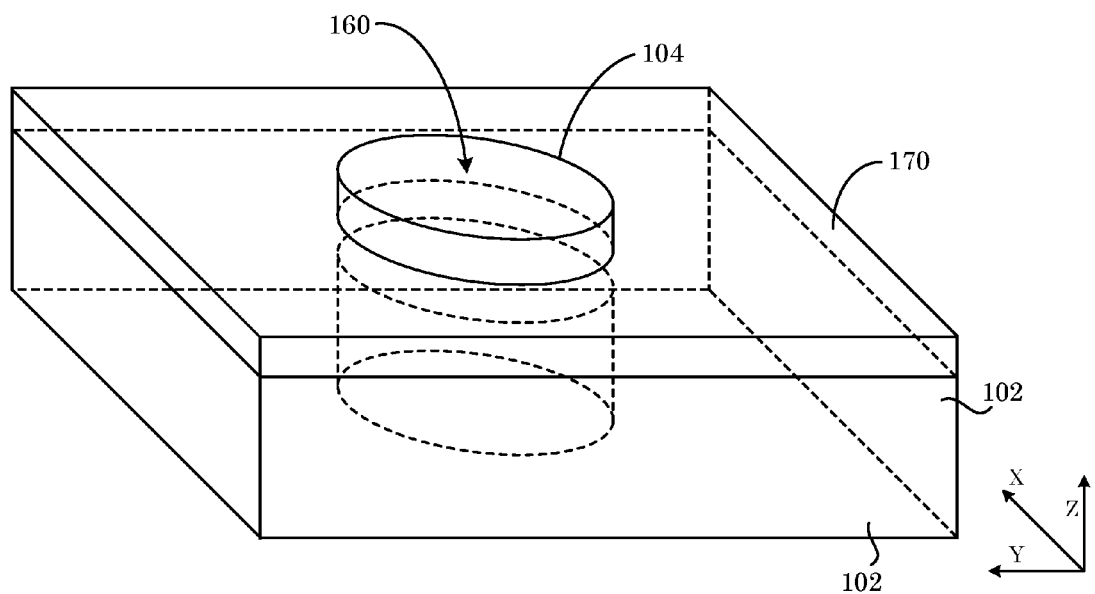
FIG. 8 shows a resonator.
Figure 8:
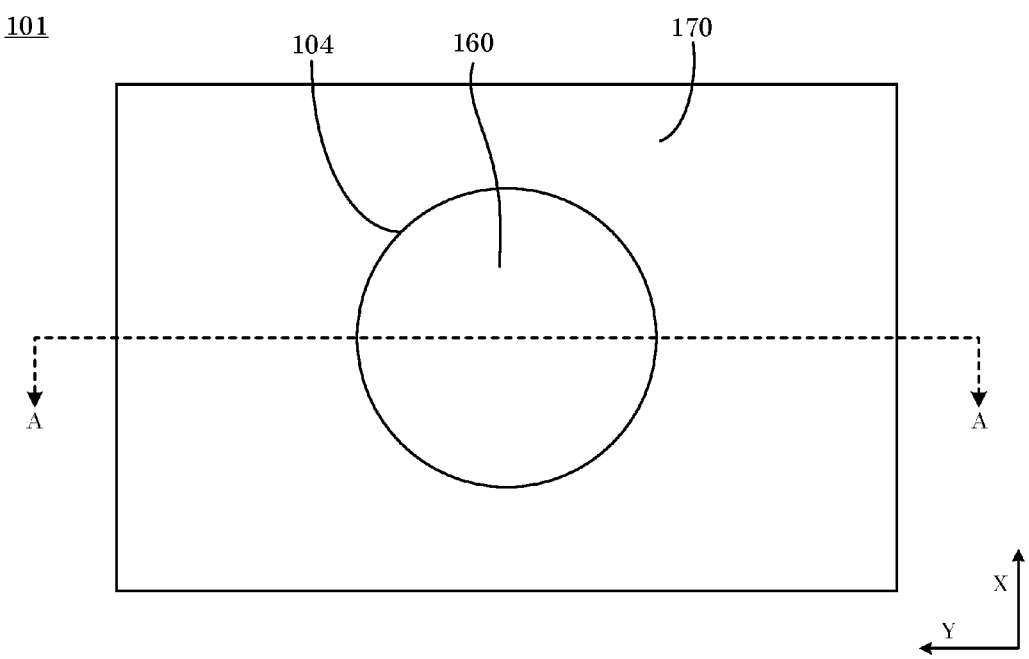
Figure 9:
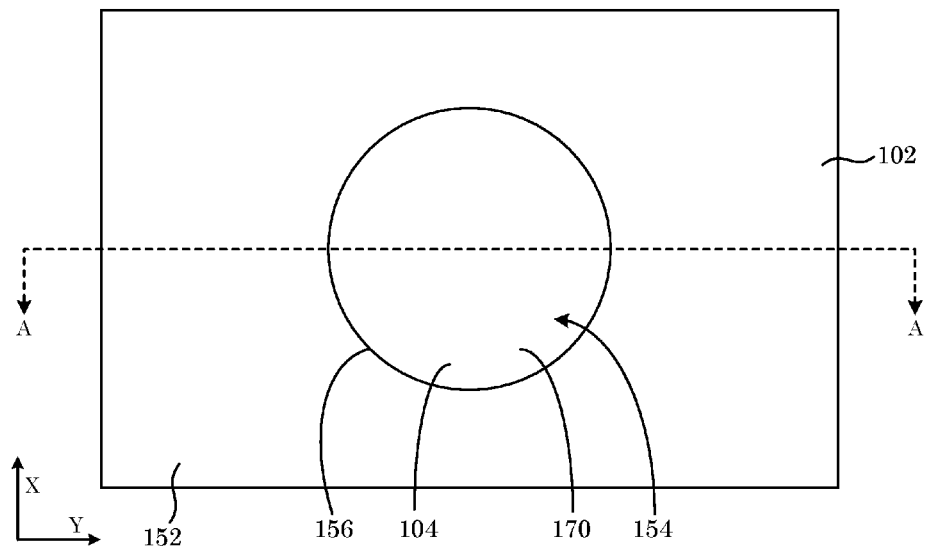
FIG. 9 shows a resonator.
Figure 9:
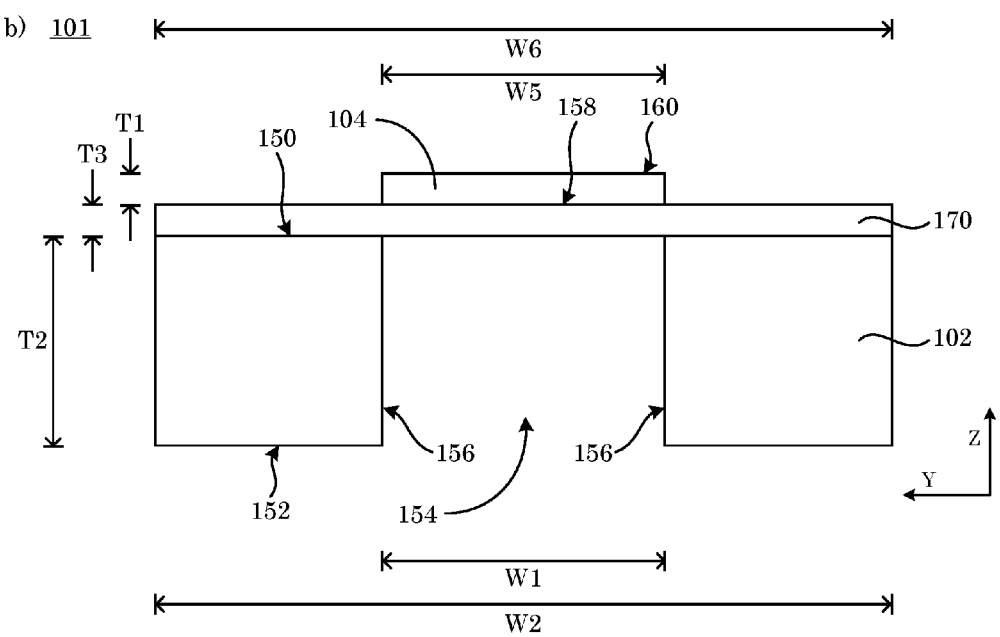

In an embodiment, with reference to FIG. 8 (panel a: perspective view; panel b: top view) and FIG. 9 (panel a: bottom view; panel b: cross-section along line A-A shown in FIG. 8), resonator 101 includes a film bulk acoustic resonator. Here, piezoelectric member 104 is disposed on substrate 102, and intermediate member 170 is interposed between piezoelectric member 104 and substrate 102. Intermediate member 170 is present at first surface 150 of substrate 102 and also present at mesa surface 158 of piezoelectric member 104. Additionally, resonator 101 includes inverted mesa 154 bounded by wall 156 of substrate 102 and intermediate member 170. Moreover, intermediate member 170 has thickness T3 and width W6.

Figure 10:
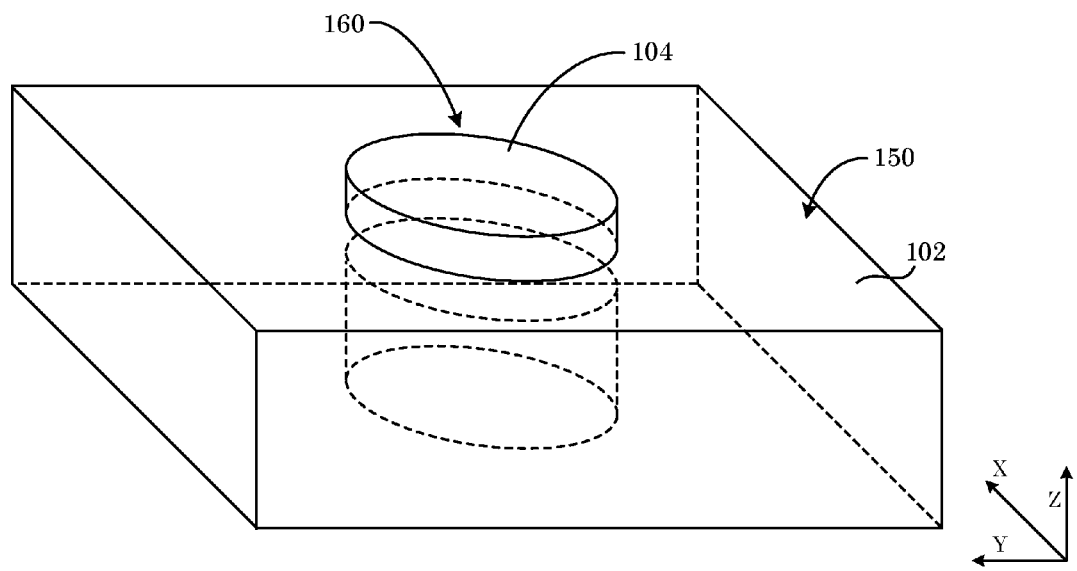
FIG. 10 shows a resonator.
Figure 10:
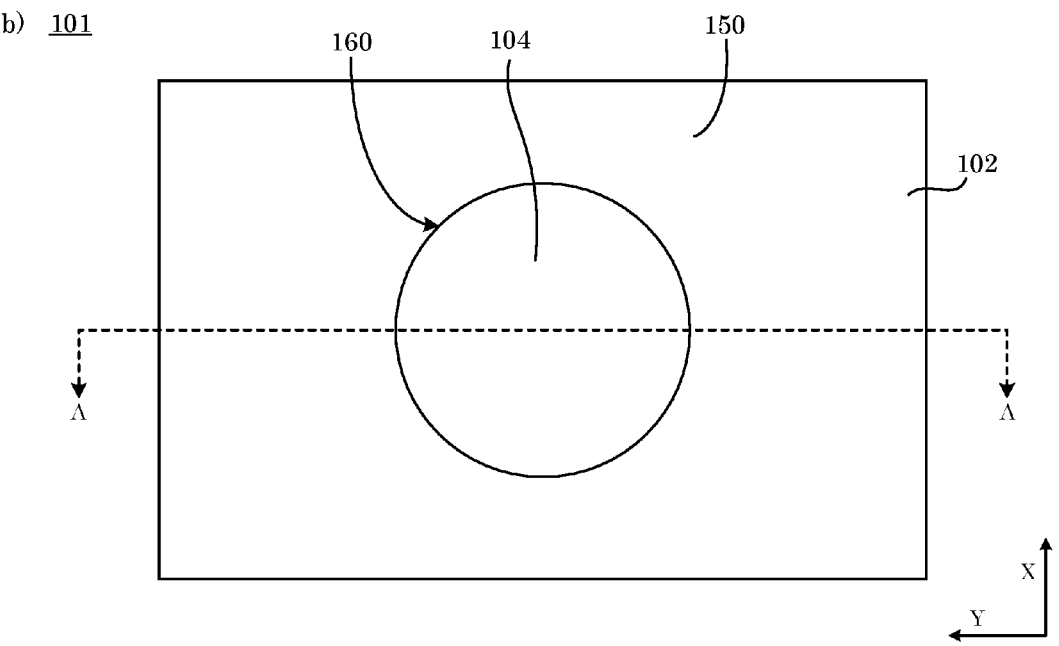
Figure 11:
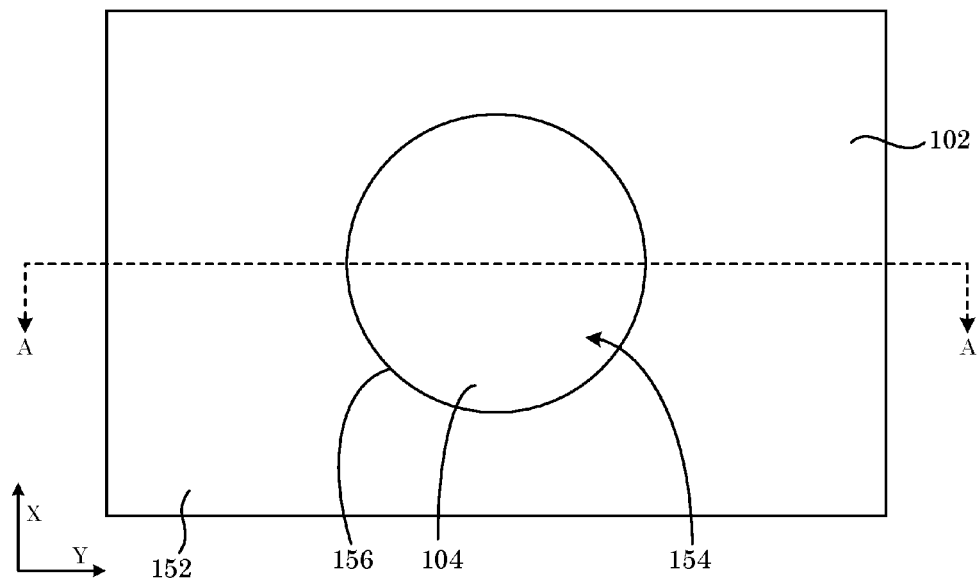
FIG. 11 shows a resonator.
Figure 11:
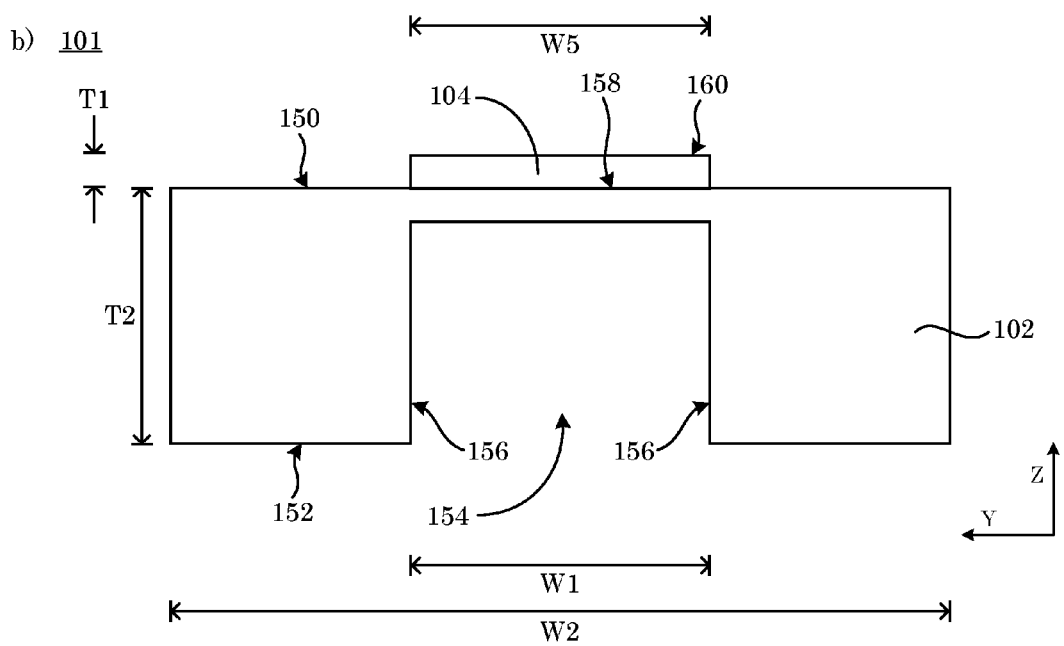

In an embodiment, with reference to FIG. 10 (panel a: perspective view; panel b: top view) and FIG. 11 (panel a: bottom view; panel b: cross-section along line A-A shown in FIG. 10), resonator 101 includes a film bulk acoustic resonator. Here, piezoelectric member 104 is stackedly disposed on substrate 102, wherein piezoelectric member 104 is present at first surface 150 that opposes second surface 152 of substrate 102. Additionally, resonator 101 includes inverted mesa 154 bounded by wall 156 of substrate 102, wherein substrate 102 is present between piezoelectric member 104 and inverted mesa 154 such that inverted mesa 154 has width W1, piezoelectric member 104 has width W5.

Figure 12:
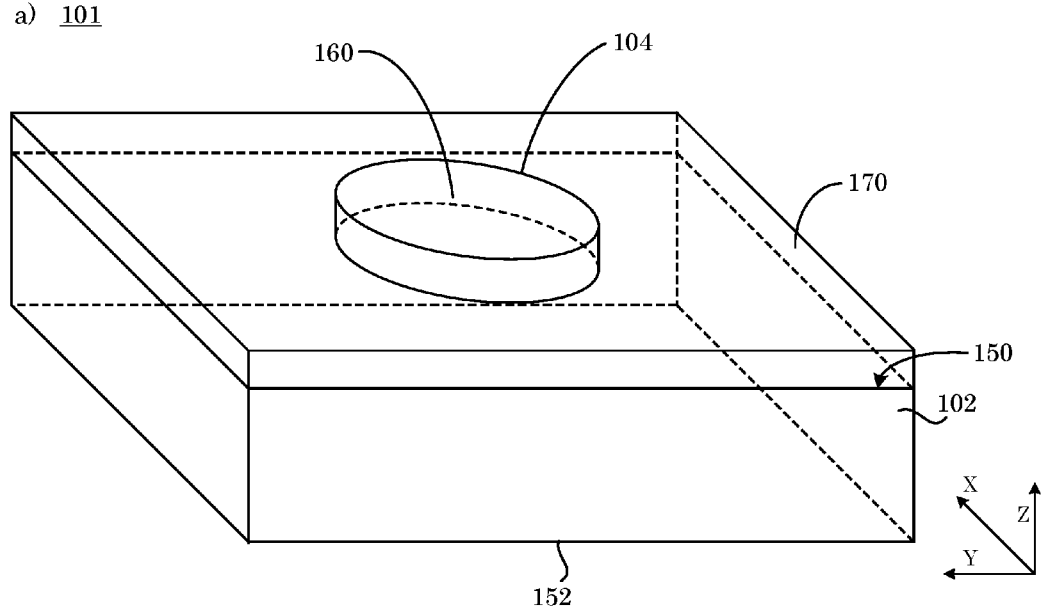
FIG. 12 shows a resonator.
Figure 12:
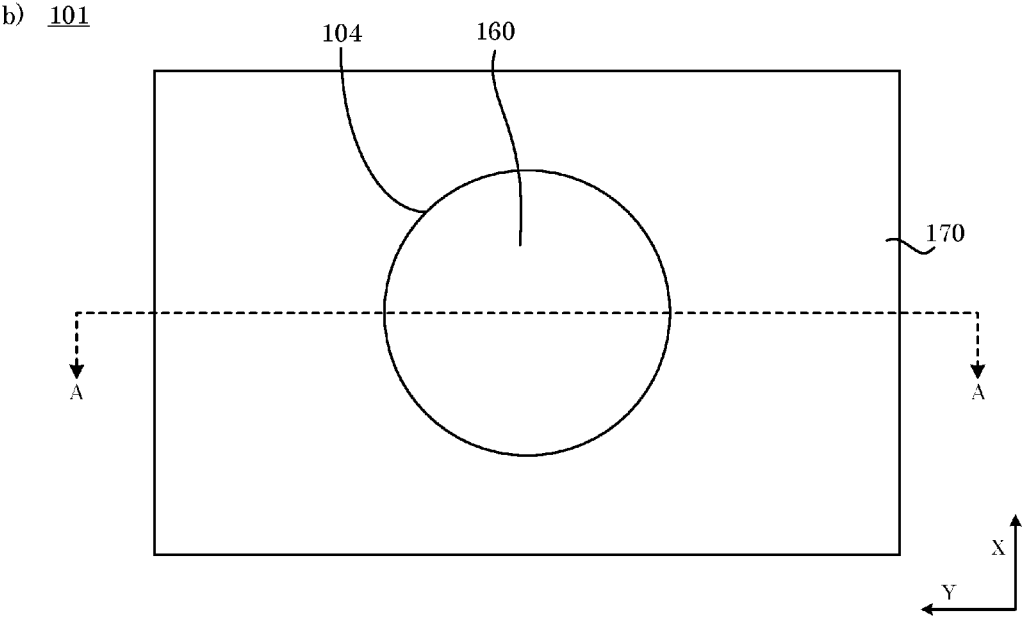
Figure 13:
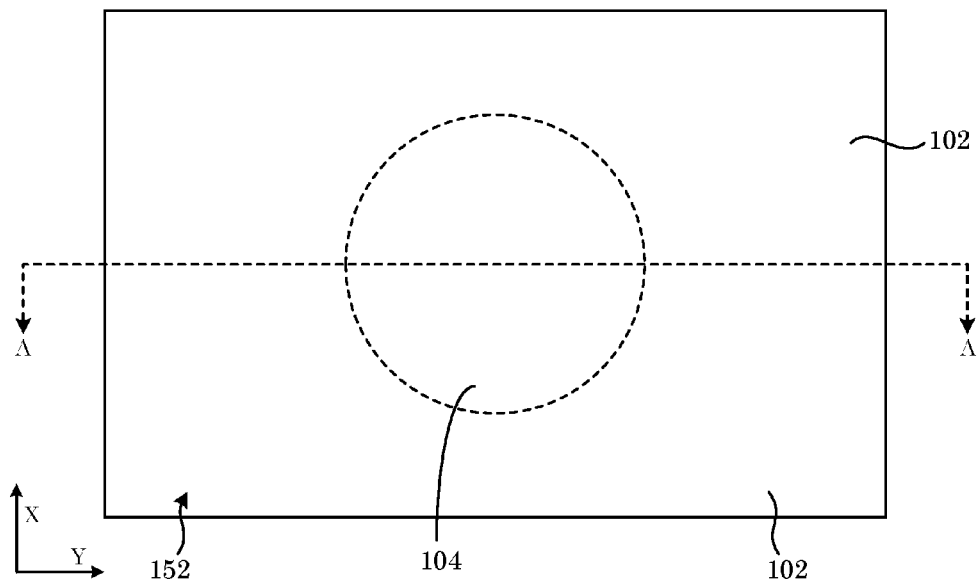
FIG. 13 shows a resonator.
Figure 13:
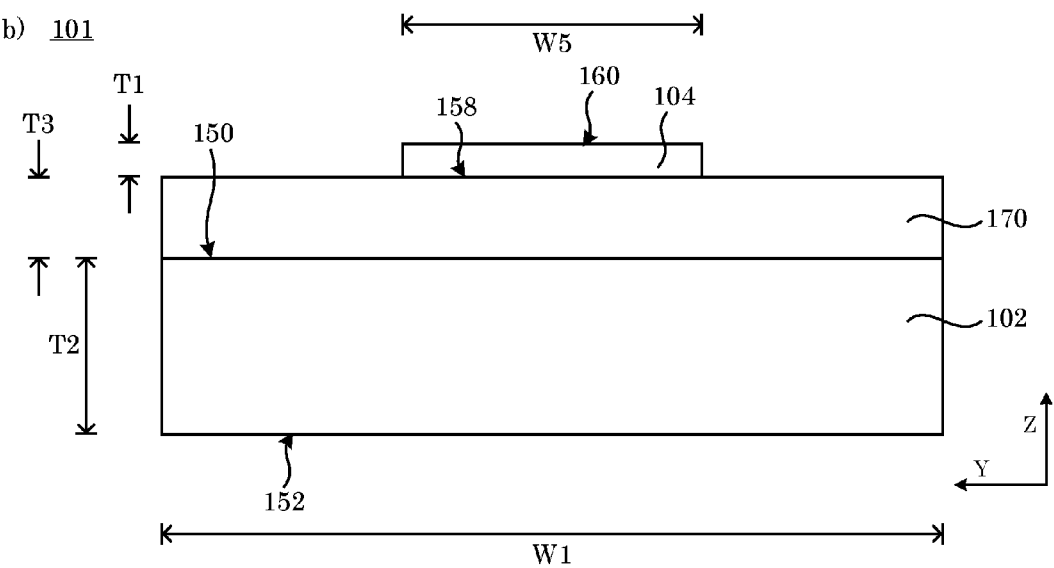

In an embodiment, with reference to FIG. 12 (panel a: perspective view; panel b: top view) and FIG. 13 (panel a: bottom view; panel b: cross-section along line A-A shown in FIG. 12), resonator 101 includes a solidly mounted bulk resonator. Here, piezoelectric member 104 is disposed on substrate 102, and intermediate member 170 is interposed between piezoelectric member 104 and substrate 102. Intermediate member 170 is present at first surface 150 of substrate 102 and also present at surface 158 of piezoelectric member 104 such that piezoelectric member 104 is exposed on a portion of intermediate member 170, and a portion of intermediate member 170 is exposed by being uncovered by piezoelectric member 104. Intermediate member 170 can have an internal structure to reflect acoustic energy emitted from piezoelectric member 104 at a specified wavelength, to reduce acoustic losses, and to enhance a quality factor Q of a resonant mode of piezoelectric member 104. An internal structure of intermediate member 170 can include alternating layers of materials (e.g., two materials) with different elastic properties arranged as a Bragg mirror for specified acoustic waves.

A shape and size of substrate 102 provides support for piezoelectric member 104, electrodes (180, 182), intermediate layer 170, or combination thereof. The shape can be rectangular, cylindrical, and the like. The size can be a millimeter to a centimeter, and the like. A thickness can be from tens of microns to a millimeter.

A shape and size of piezoelectric member 104 is selected to produce acoustic vibrations response to excitation by electrodes (180, 182). The shape can be circular, rectangular, polygonal, or any other open geometry. The size can be tens of microns to a centimeter. A thickness can be a micron to a millimeter.

Figure 14:
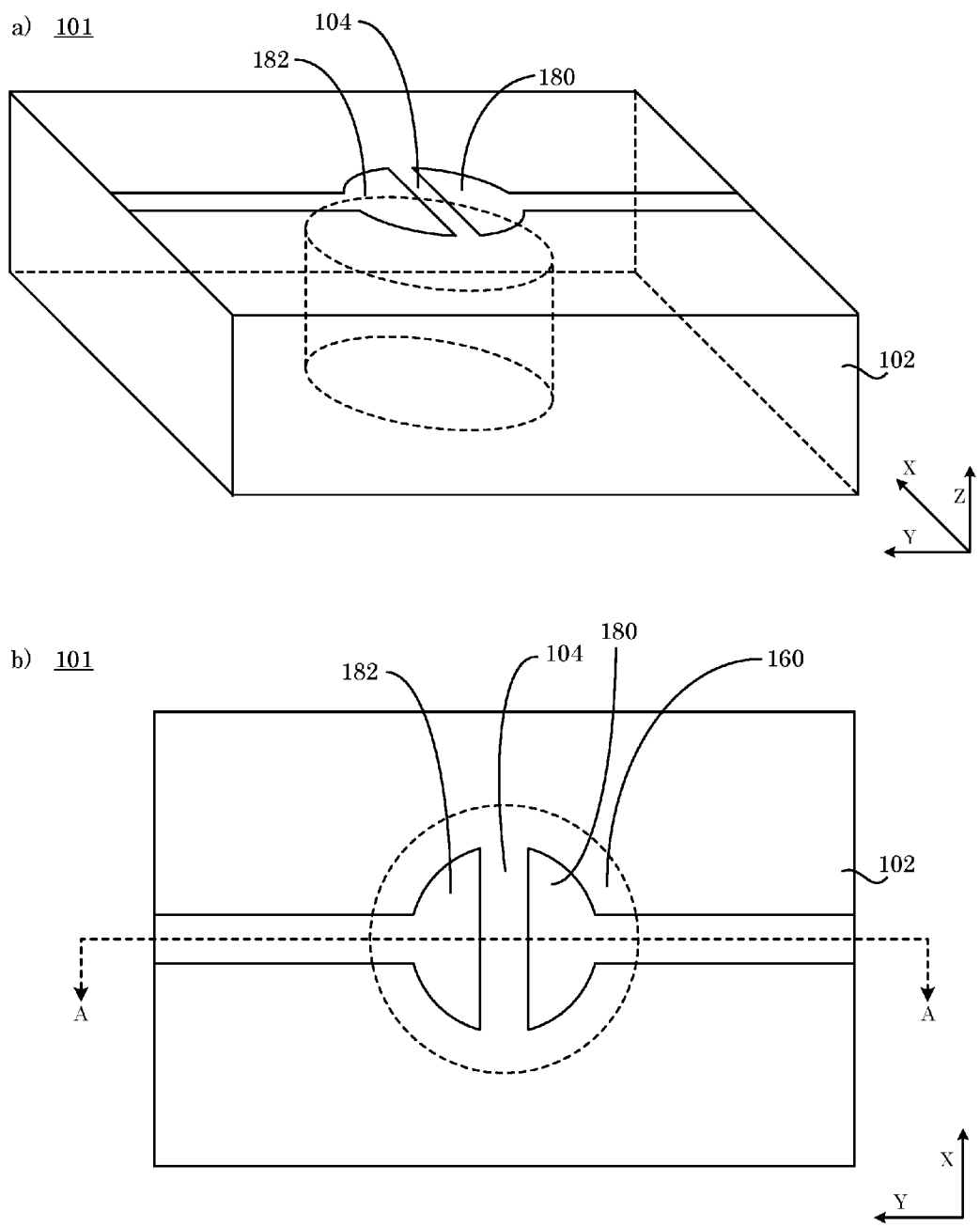
FIG. 14 shows electrodes disposed on a piezoelectric member of a resonator.
Figure 15:
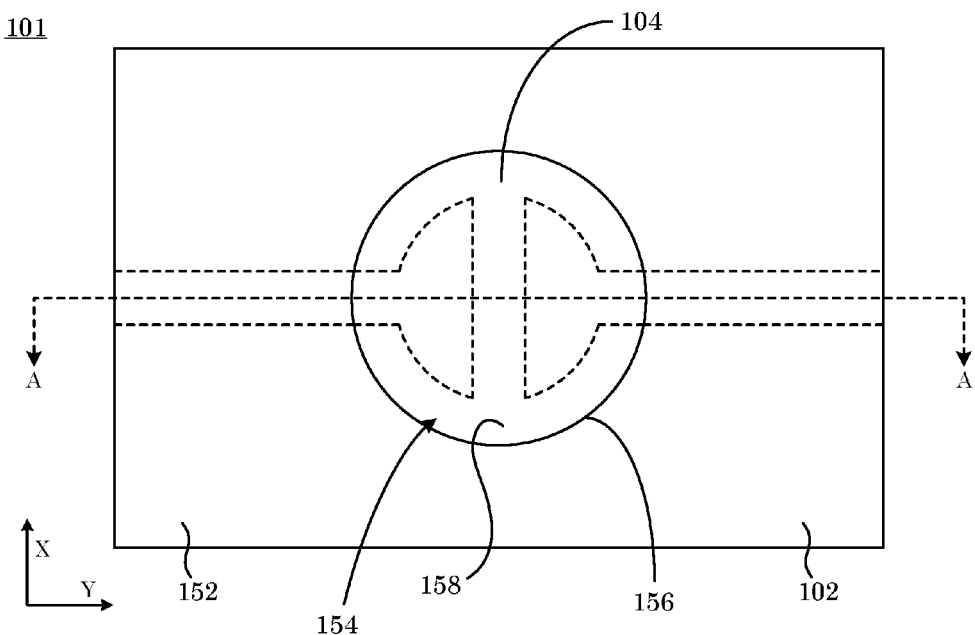
FIG. 15 shows electrodes disposed on a piezoelectric member of a resonator.
Figure 15:
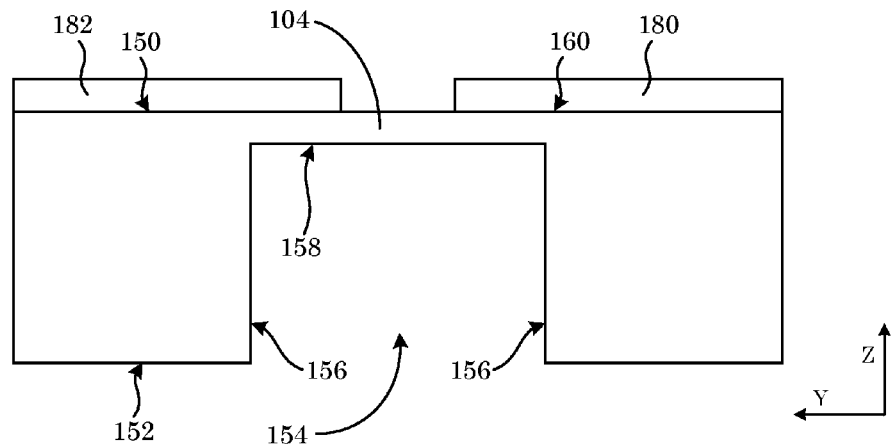
Figure 18:
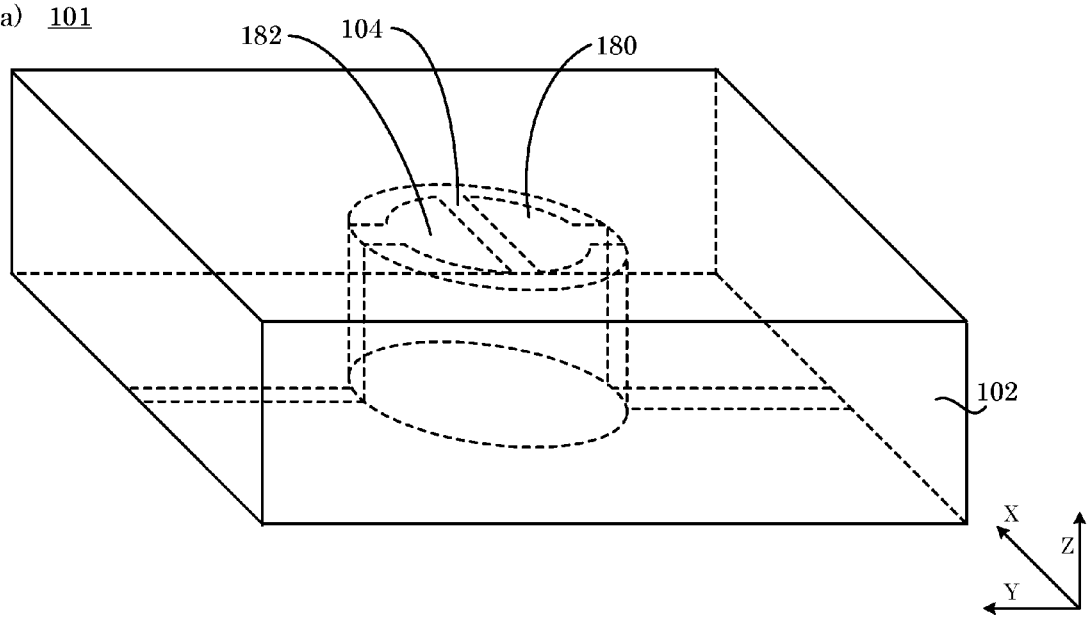
FIG. 18 shows electrodes disposed on a piezoelectric member of a resonator.
Figure 18:
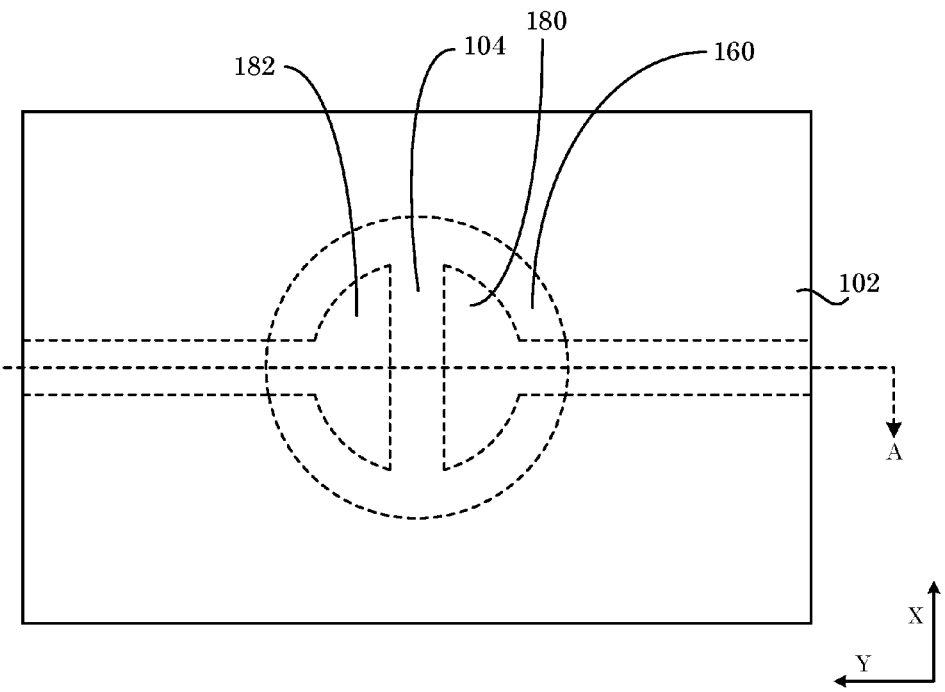
Figure 19:
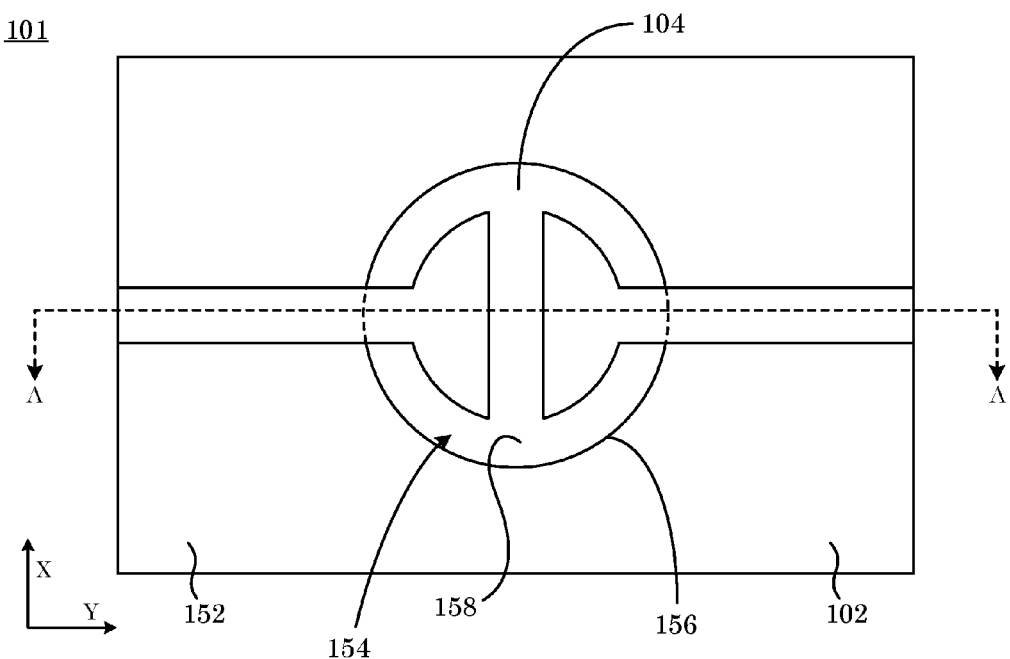
FIG. 19 shows electrodes disposed on a piezoelectric member of a resonator.
Figure 19:
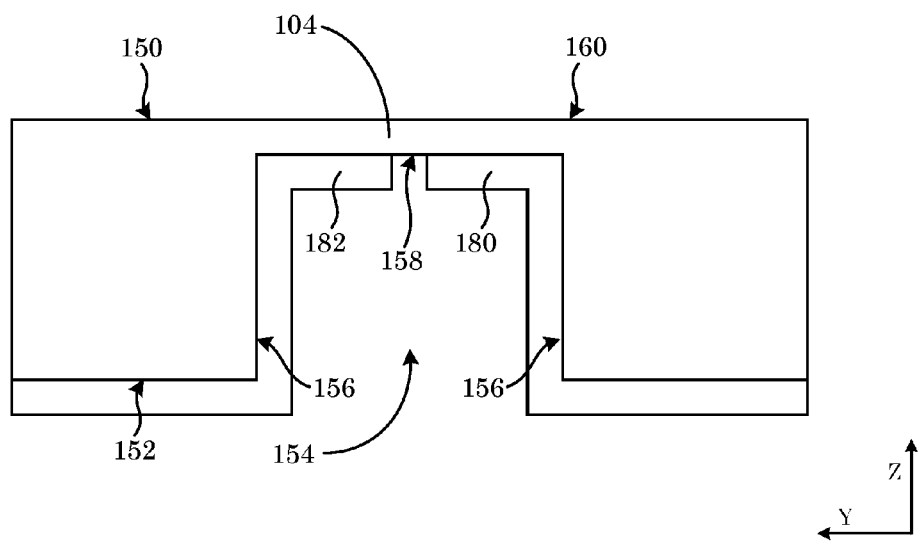

Electrodes are disposed on piezoelectric member 104 to excite vibration of piezoelectric member 104. In an embodiment, as shown in FIG. 14 (panel a: perspective view; panel b: top view) and FIG. 15 (panel a: bottom view; panel b: cross-section along line A-A shown in FIG. 14), first electrode 180 and second electrode 182 are disposed on a same surface of substrate 102, e.g., second surface 150. Similarly, first electrode 180 and second electrode 182 can be disposed on first surface 152 of substrate 102 and also disposed in inverted mesa 154 as shown in FIG. 18 (panel a: perspective view; panel b: top view) and FIG. 19 (panel a: bottom view; panel b: cross-section along line A-A shown in FIG. 18). In this arrangement, first electrode 180 and second electrode 182 provide electric field excitation of piezoelectric member 104, wherein an electric field produced by first electrode 180 and second electrode 182 is substantially in a plane of piezoelectric member 104. Moreover, a crystallographic orientation of piezoelectric member 104 with respect to the electric field provides lateral field excitation of thickness-shear strain in piezoelectric member 104 produced in response to the electric field.

Figure 16:
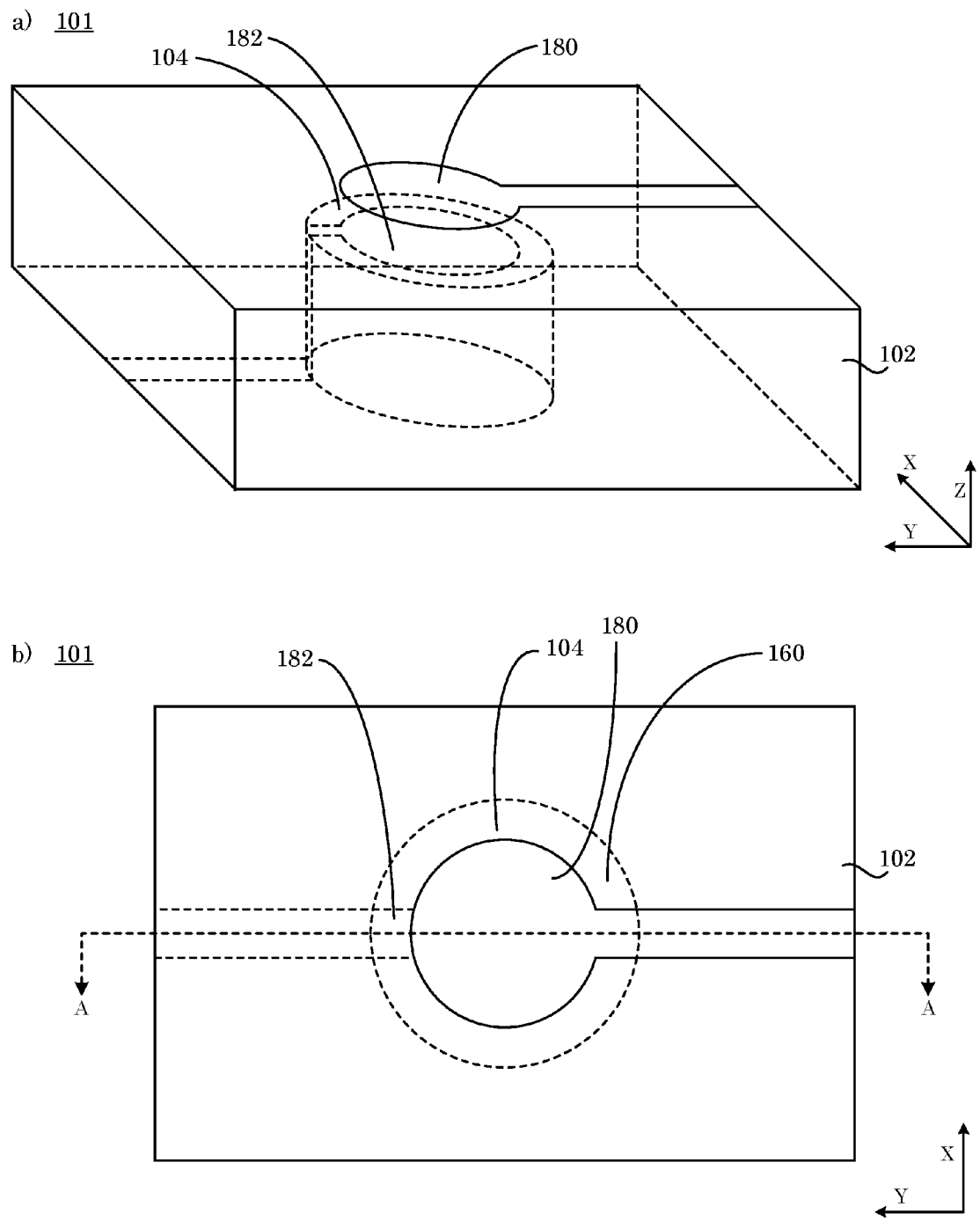
FIG. 16 shows electrodes disposed on a piezoelectric member of a resonator.
Figure 17:
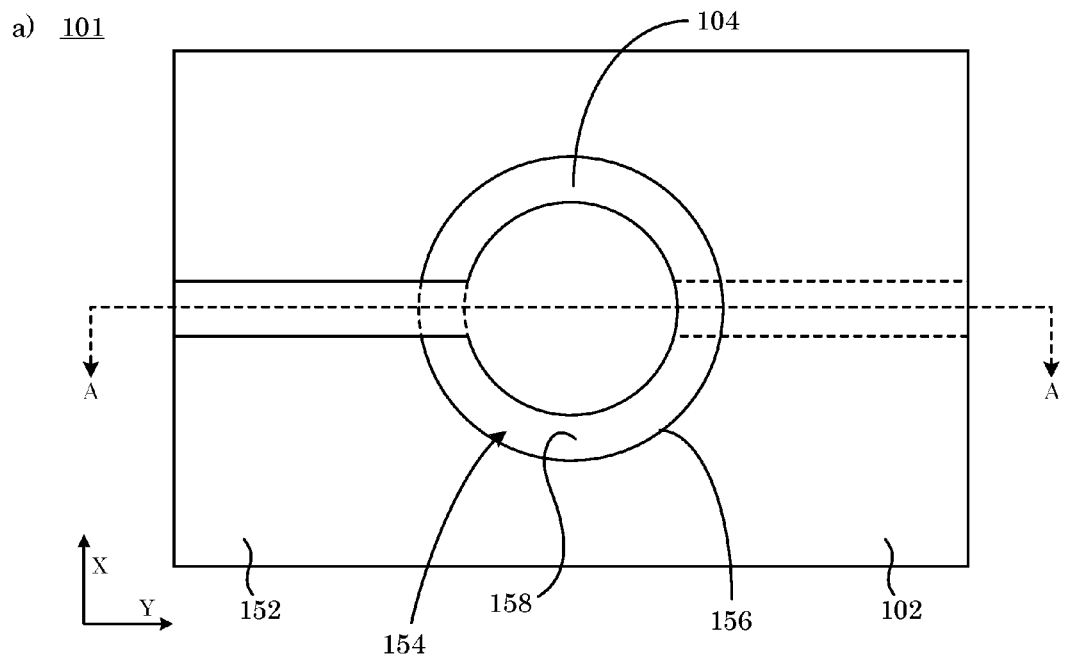
FIG. 17 shows electrodes disposed on a piezoelectric member of a resonator.
Figure 17:
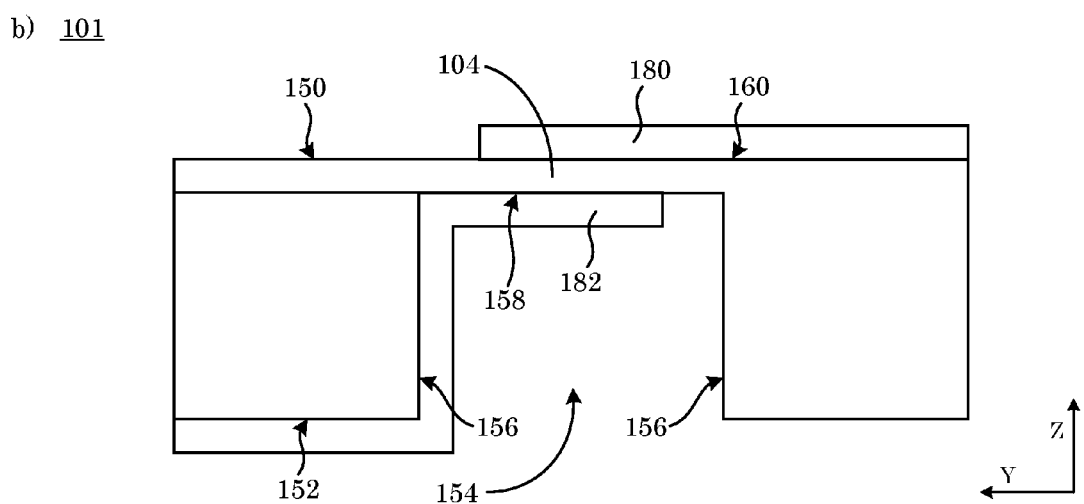

According to an embodiment, as shown in FIG. 16 (panel a: perspective view; panel b: top view) and FIG. 17 (panel a: bottom view; panel b: cross-section along line A-A shown in FIG. 16), first electrode 180 and second electrode 182 are disposed on a different surface of substrate 102 such as first electrode 180 being disposed on second surface 152 and second electrode 182 being disposed on first surface 150 of substrate 102. Here, a portion of first electrode 180 and second electrode 182 overlap on substrate 102 to excite vibration of piezoelectric member 104. In this arrangement, first electrode 180 and second electrode 182 provide electric field excitation of piezoelectric member 104, wherein an electric field produced by first electrode 180 and second electrode 182 is substantially normal to basal surface 160 and mesa surface 158 of piezoelectric member 104. Moreover, a crystallographic orientation of piezoelectric member 104 with respect to the electric field provides thickness-shear strain in piezoelectric member 104 produced in response to the electric field.

Figure 20:
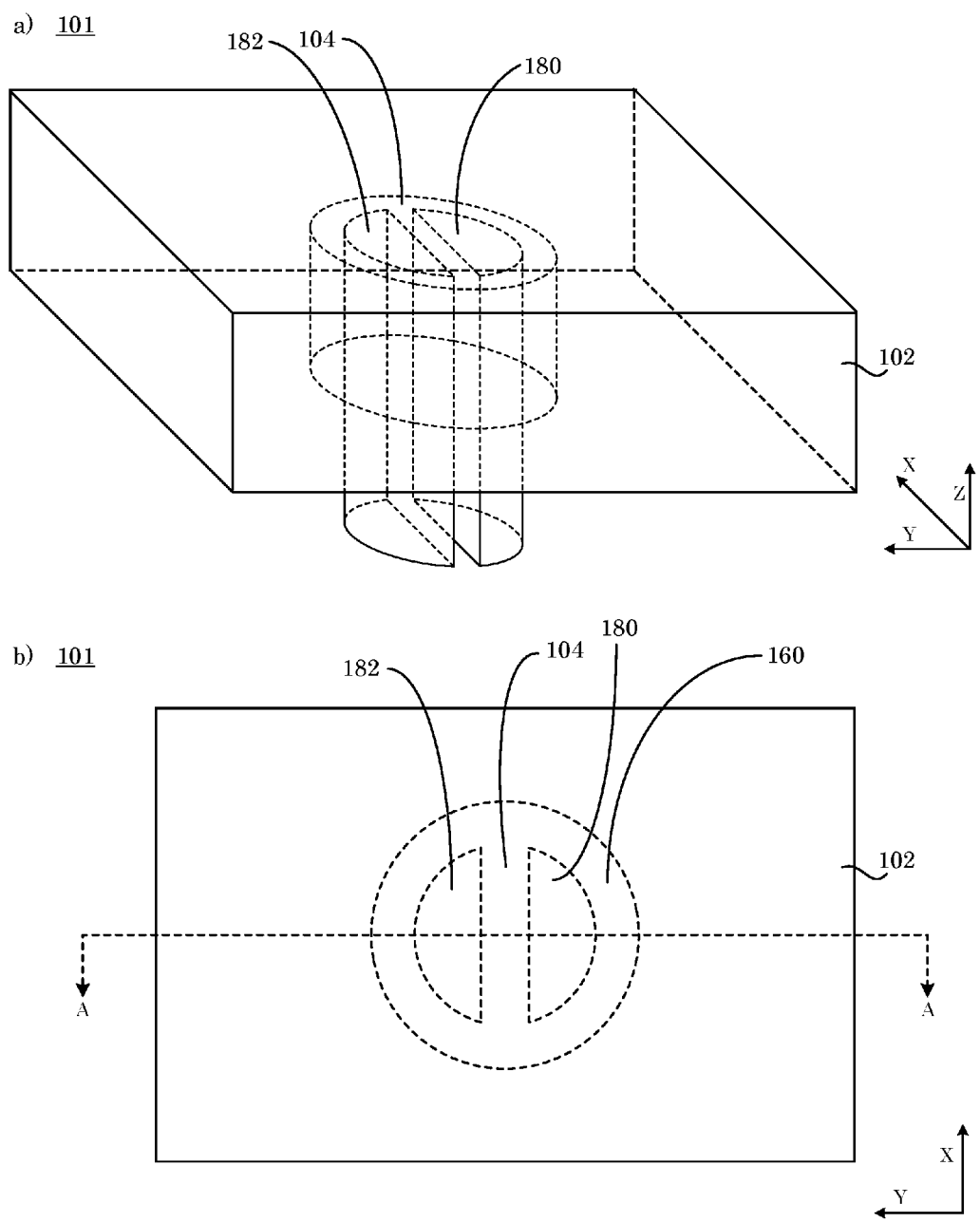
FIG. 20 shows electrodes disposed on a piezoelectric member of a resonator.
Figure 21:
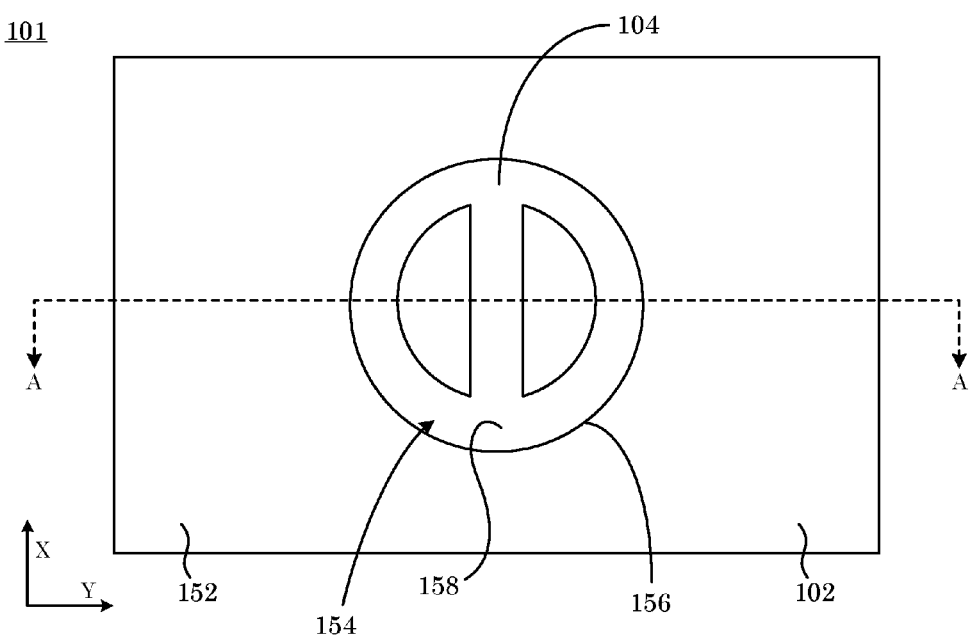
FIG. 21 shows electrodes disposed on a piezoelectric member of a resonator.
Figure 21:
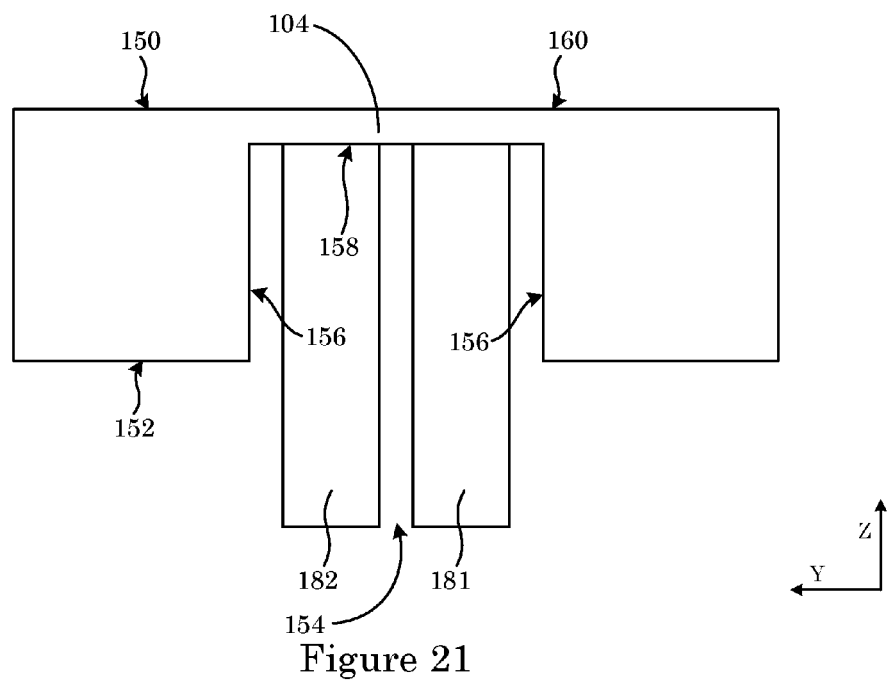

In an embodiment, as shown in FIG. 20 (panel a: perspective view; panel b: top view) and FIG. 21 (panel a: bottom view; panel b: cross-section along line A-A shown in FIG. 20), first electrode 180 and second electrode 182 provide lateral field excitation to piezoelectric member 104, wherein first electrode 180 and second electrode 182 are proximately disposed to piezoelectric member 104 but not contacting a surface of piezoelectric member 104 such that a gap exists interposed between electrodes (180, 182) and piezoelectric member 104 in a non-contact configuration. It is contemplated that similar non-contacting configurations of electrodes can be included in embodiments such as those shown in FIG. 14, FIG. 15, FIG. 16, FIG. 17, FIG. 18, FIG. 19, and the like. Accordingly, in the non-contact configuration, electrodes (180, 182) can be disposed proximate to (but out of contact with) piezoelectric member 104; or one electrode of electrodes (180, 182) can be non-contacting while the other contacts piezoelectric member 104. In an embodiment, electrodes (180, 182) shown in FIG. 16 and FIG. 17 is modified such that second electrode 180 is a non-contacting electrically conductive post disposed proximate to mesa surface 158 of piezoelectric member 104.

A shape of electrodes (180, 182) can be the same or different and can be independently selected such that a combination of first electrode 180 and second electrode 182 excites vibration of piezoelectric member 104 in response to a potential difference being subjected to electrodes (180, 182). The outer borders of the sections of the two electrodes over piezoelectric member 104, not including lead sections from the surrounding substrate can be circular, rectangular, and the like, and additionally have a gap between the electrodes close to the center of the piezoelectric member. The shapes of lead electrode sections are of arbitrary shape, except that the two sections do not touch. The size of the sections of electrodes (180, 182) over the piezoelectric member independently can be from one tenth to one times the size of the piezoelectric member. A thickness (normal to a surface of piezoelectric member 104) of electrodes (180, 182) independently can be from 100 nm to several microns, if adhered to the piezoelectric member, or of any thickness if not adhered to the piezoelectric member.

Resonator 101 receives a sample, e.g., a biological sample, reference sample, and the like disposed on piezoelectric member 104. In an absence of sample, piezoelectric member 104 produces acoustic vibrations in response to subjecting electrodes (180, 182) disposed on piezoelectric member 104 to an excitation signal, e.g., from an excitation source. The acoustic vibration of piezoelectric member 104 has a phase noise signal, which changes in a presence of sample and that can also change due to a motion of the sample on piezoelectric member 104. The sample can be disposed on piezoelectric member 104 in a number of ways. In an embodiment, with reference to FIG. 22 (panel a: perspective view; panel b: exploded view), FIG. 23 (panel a: top view; panel b: cross-sectional view along line A-A shown in top view), FIG. 24 (panel a: perspective view; panel b: exploded view), FIG. 25 (panel a: top view; panel b: cross-sectional view along line A-A shown in top view), and FIG. 26 (cross-sectional view), acoustic article 100 can include resonator 101 in fluid communication with container member 188 such that fluid reservoir 184 is interposed between container member 108 and piezoelectric member 104 of resonator 101. Here, fluid in fluid reservoir 184 can contact piezoelectric member 104 of resonator 101. Container member 188 includes wall 186 two bound fluid reservoir 184, inlet channel 190 bounded by wall 192 to provide fluid (e.g., a sample) into fluid reservoir 184, outlet channel 196 bounded by wall 194 to communicate fluid from fluid reservoir 184, and optionally including seal 198 interposed between container member 188 and resonator 101 to seal container member 188 to resonator 101. Seal 198 can be a gasket, O-ring, or other seal including an adhesive or bonding agent. Exemplary materials for seal 108 include an elastomer, cross-linkable polymer (e.g., cyanoacrylates), silicone adhesives, low temperature metal alloy bonding agents, and the like. The fluid can be communicated and disposed in fluid reservoir 184 so that the fluid is statically present in fluid reservoir 184 or actively flowed therethrough. Moreover, a flow of the fluid can be intermittently terminated with fluid disposed in fluid reservoir 184, and the flow recommended for delivery of additional fluid into fluid reservoir 184 or removal of fluid from fluid reservoir 184.

Figure 22:
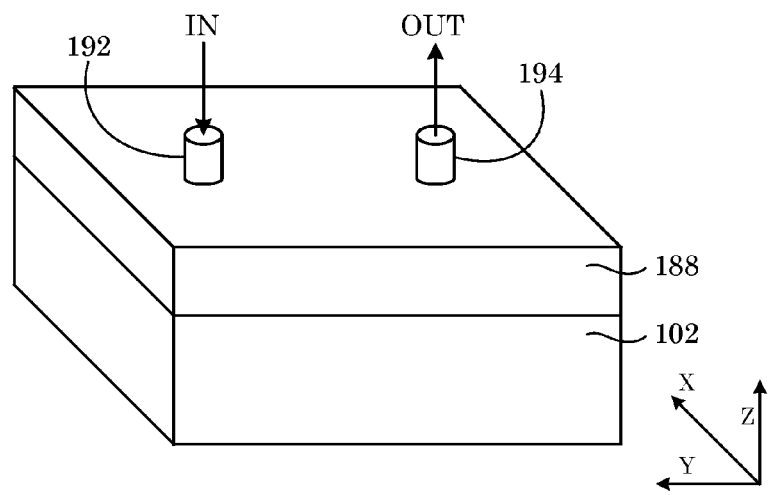
FIG. 22 shows fluid channels and fluid reservoir proximate to piezoelectric member of a resonator.
Figure 22:
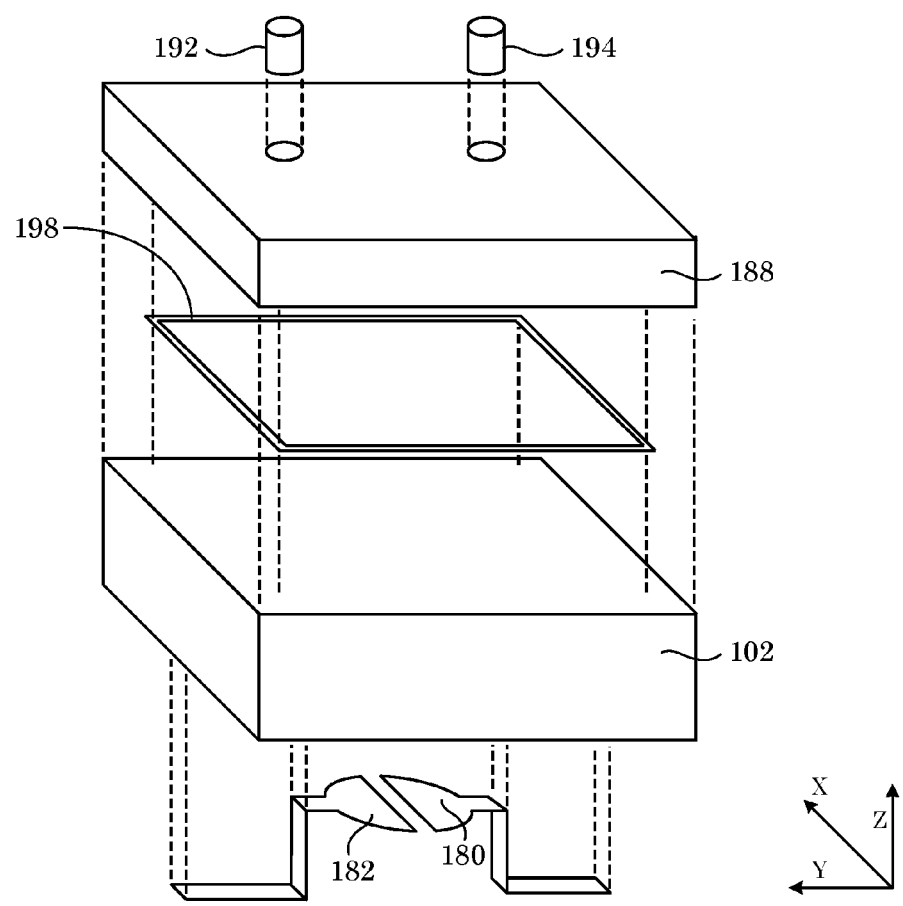
Figure 23:
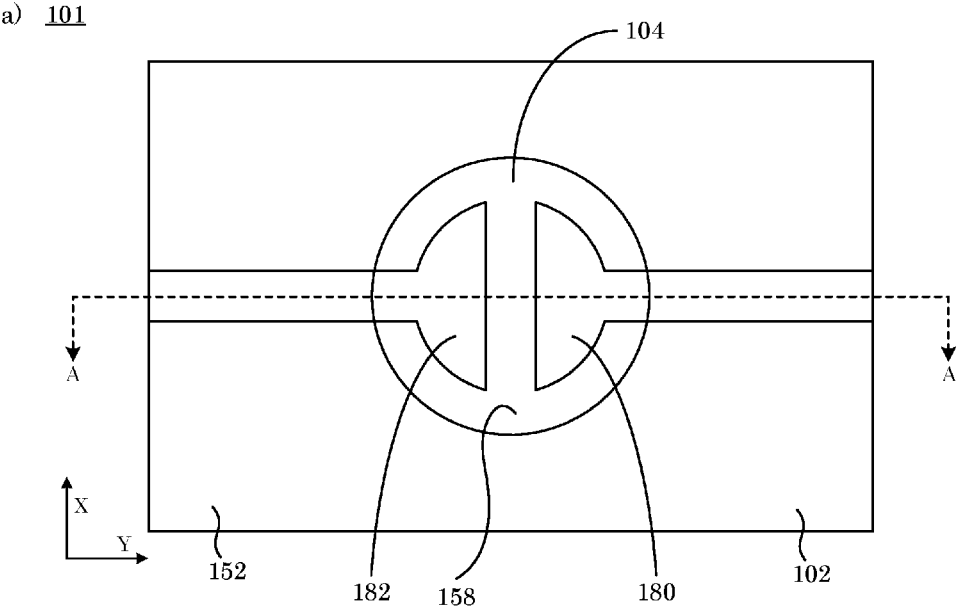
FIG. 23 shows fluid channels and fluid reservoir proximate to piezoelectric member of a resonator.
Figure 23:
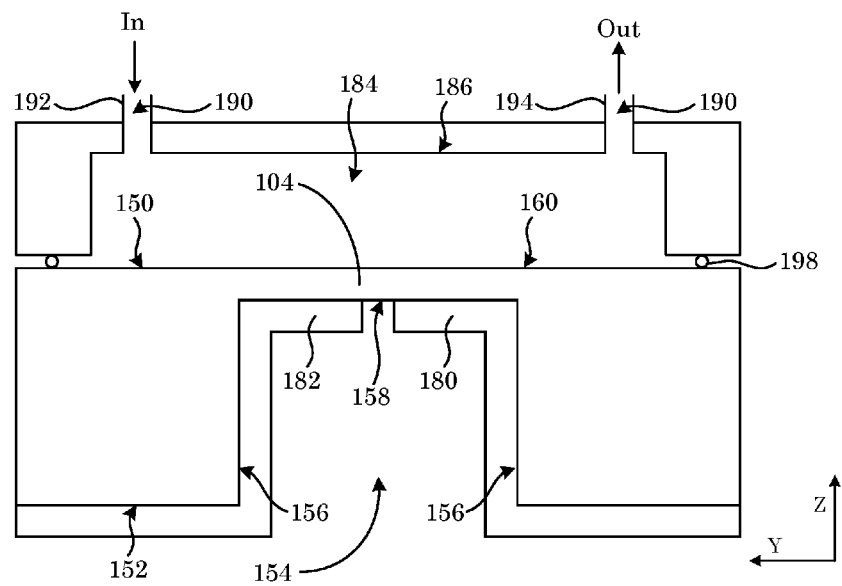
Figure 24:
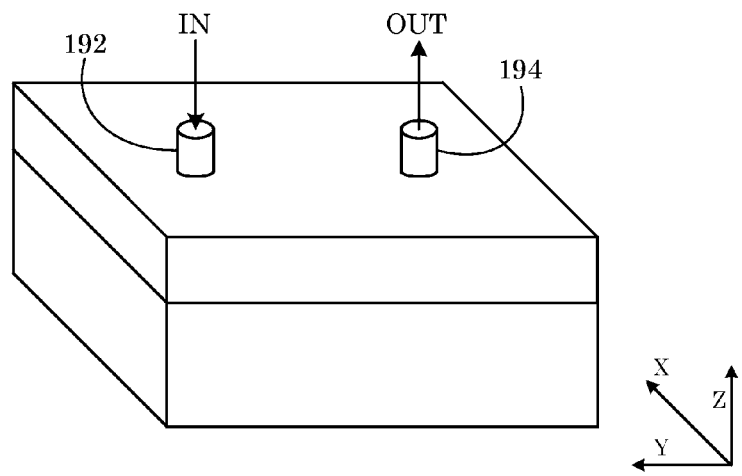
FIG. 24 shows fluid channels and fluid reservoir proximate to piezoelectric member of a resonator.
Figure 24:
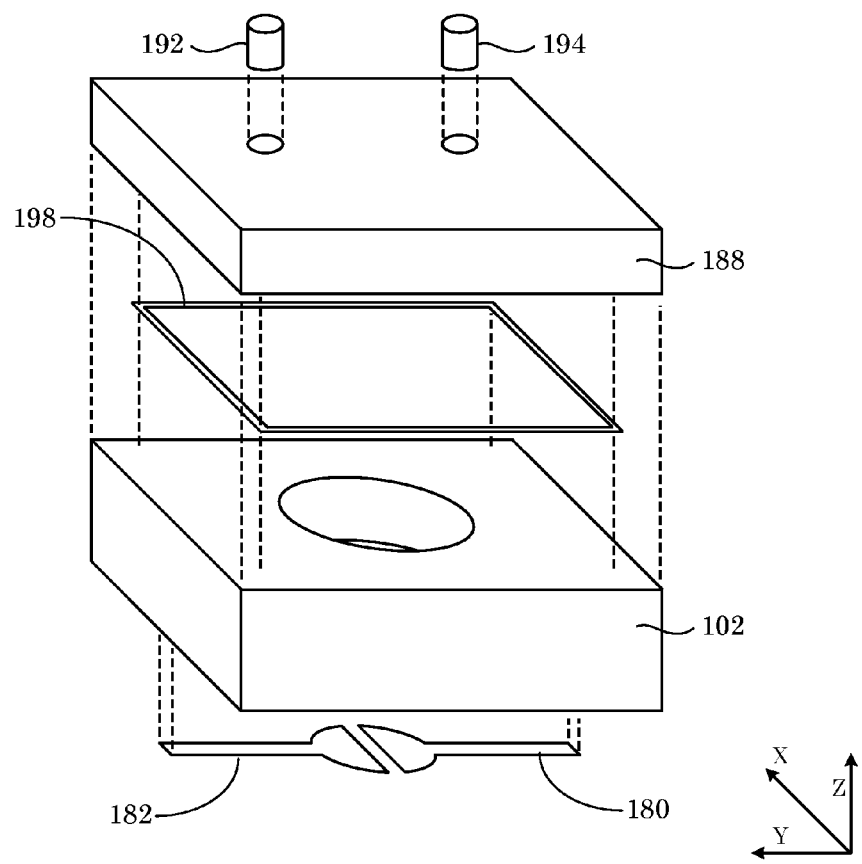
Figure 25:
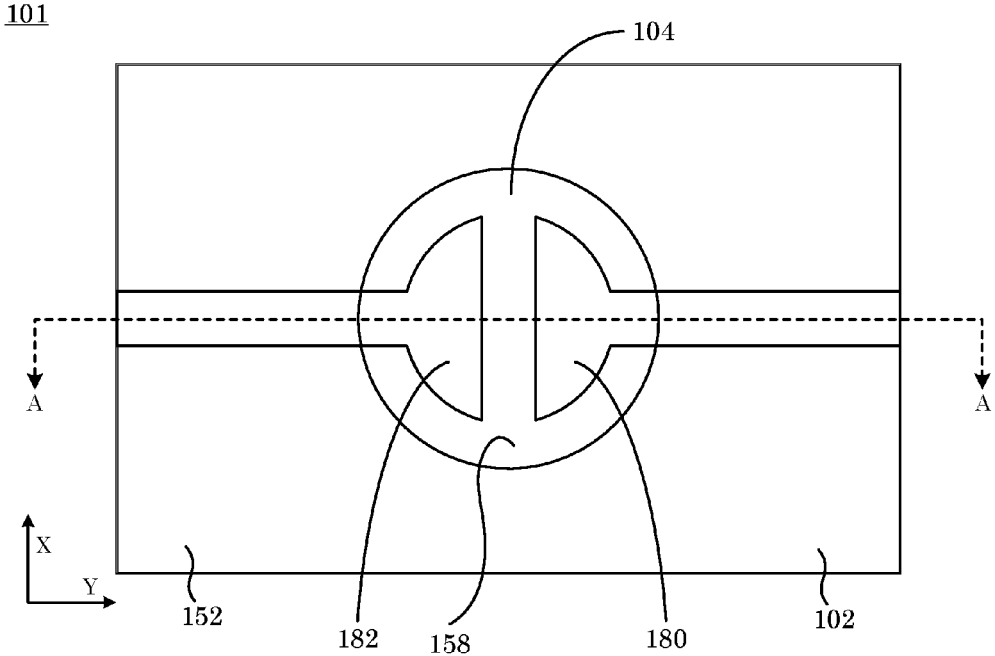
FIG. 25 shows fluid channels and fluid reservoir proximate to piezoelectric member of a resonator.
Figure 25:
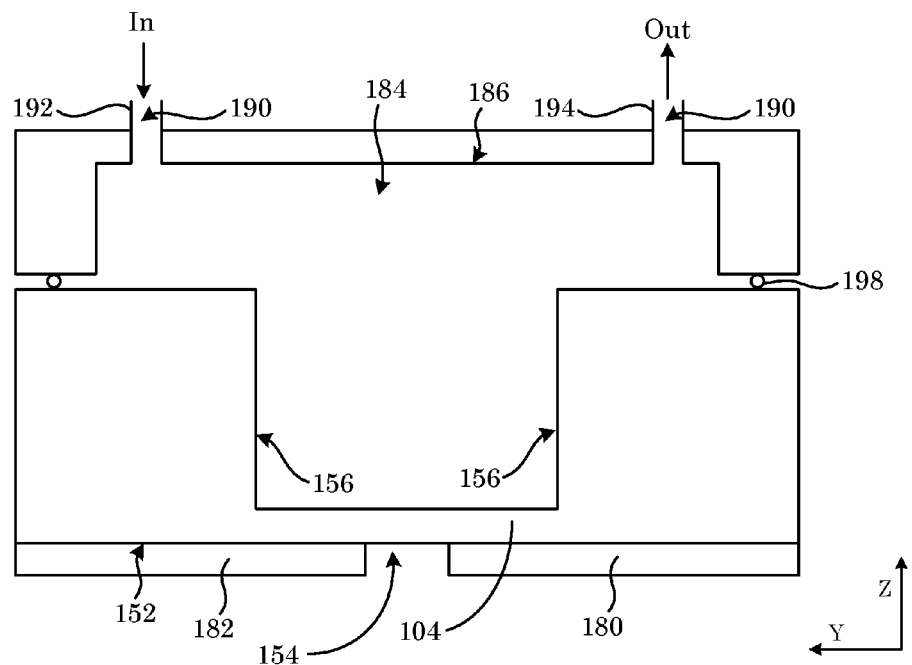
Figure 26:
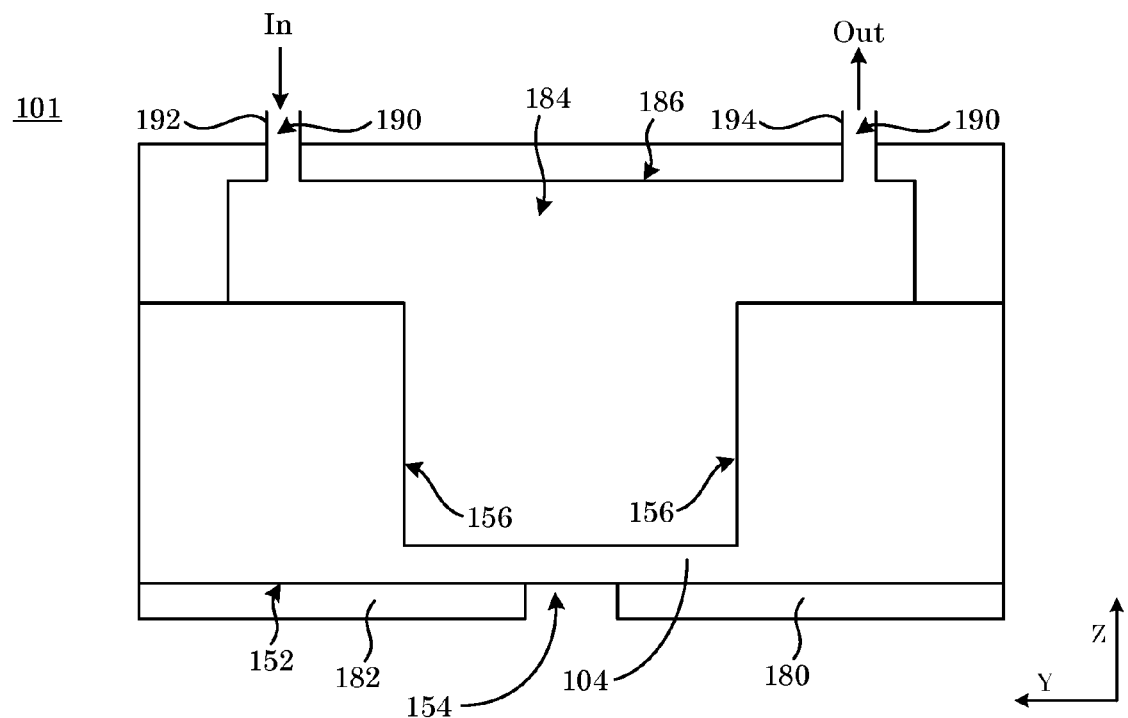
FIG. 26 shows fluid channels and fluid reservoir proximate to piezoelectric member of a resonator.

In an embodiment, as shown in FIG. 22 and FIG. 23, fluid reservoir 184 is proximate to basal surface 160 piezoelectric member 104 and distal to mesa surface 150 of is electric member 104. In some embodiments, as shown in FIG. 24 and FIG. 25, fluid reservoir 184 is distal to basal surface 160 piezoelectric member 104 and proximate to mesa surface 150 of is electric member 104. In certain embodiments, seal 198 is absent such that container member 188 disposed abuts resonator 101. It is contemplated that container member 188 and resonator 101 can be a monolithic article or can be separate components of the acoustic article 100. Moreover, electrodes (108, 110, 180, 182) for piezoelectric member 104 can be disposed in fluid reservoir 184 or can be disposed outside of fluid reservoir 184.

A shape and size of container member 188 is selected to provide fluid communication into fluid reservoir 184 and disposition of a sample onto piezoelectric member 104. The shape can be of any form that does not induce substantial spatial variations in the flow rate over the central acoustically active region of the resonator. The volume of fluid reservoir 184 can be a milliliter or less. Additionally, a flow rate of fluid through fluid reservoir 184 can be from microliters per minute to milliliters per minute, specifically from 1 microliter per minute to 1 milliliter per minute, depending on the volume of the fluid reservoir, and more specifically from 0.1 milliliters per minute to 0.4 milliliters per minute for a reservoir with volume of 0.1 milliliters.

Figure 27:
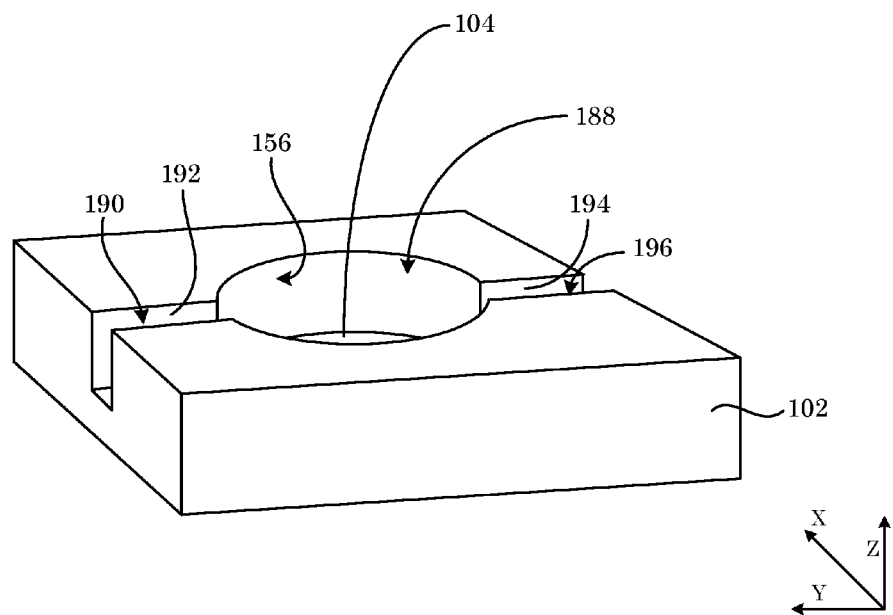
FIG. 27 shows fluid channels and fluid reservoir proximate to piezoelectric member of a resonator.
Figure 27:
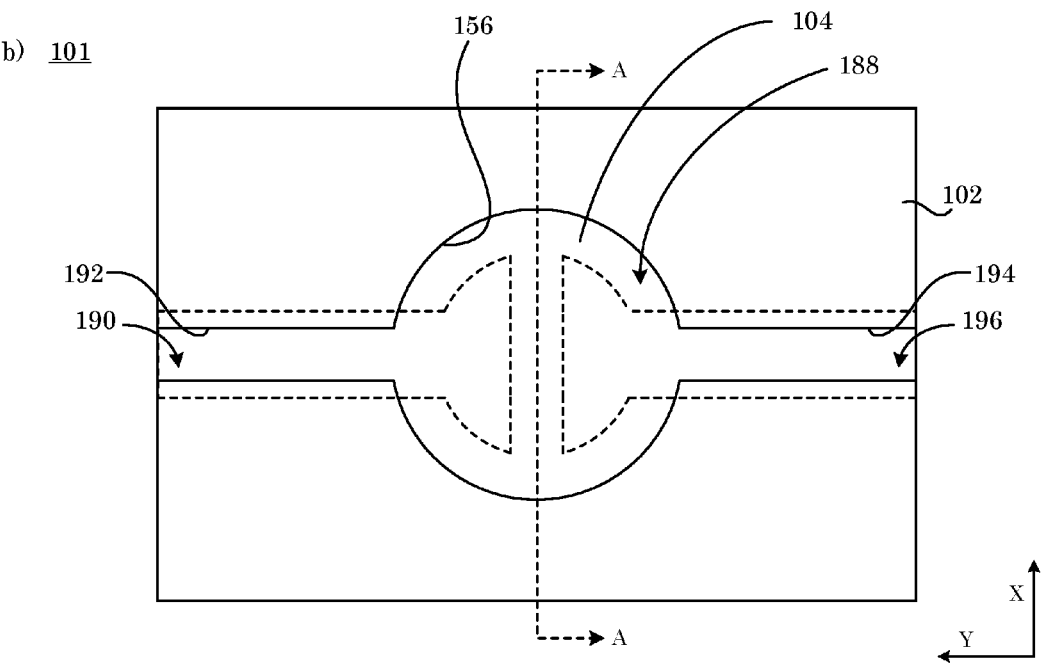
Figure 28:
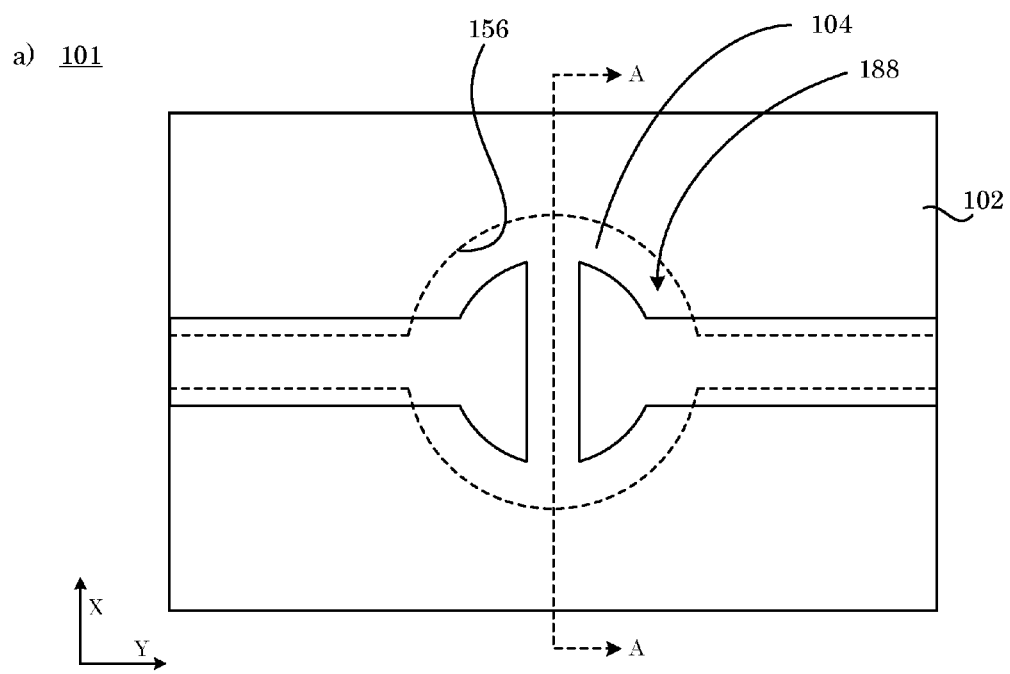
FIG. 28 shows fluid channels and fluid reservoir proximate to piezoelectric member of a resonator.
Figure 28:
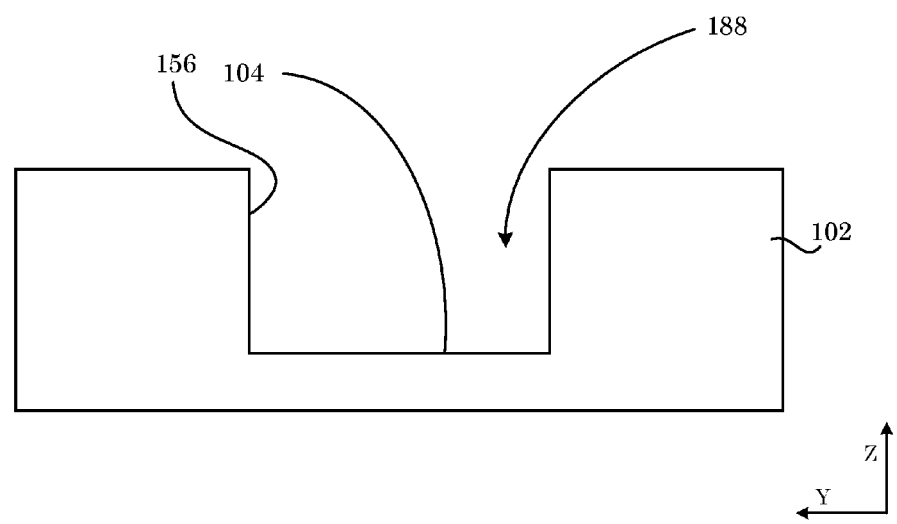

In an embodiment, inlet channel 190 or outlet channel 196 are integrated as part of resonator 101. Here, as shown in to FIG. 27 (panel a: perspective view; panel b: top view), FIG. 28 (panel a: bottom view; panel b: cross-sectional view along line A-A shown in bottom view), inlet channel 190 is disposed in substrate 102 to provide fluid communication into fluid reservoir 184, and outlet channel 196 is disposed in substrate 102 to provide fluid communication from fluid reservoir 184. In a particular embodiment, substrate 102 includes a single crystal, and inlet channel 190 or outlet channel 196 is formed in substrate 102 by etching a single crystal to remove material to form inlet channel 190 or outlet channel 196. A cover (not shown) can be disposed on substrate 102 to cover fluid reservoir 184.

Figure 29:
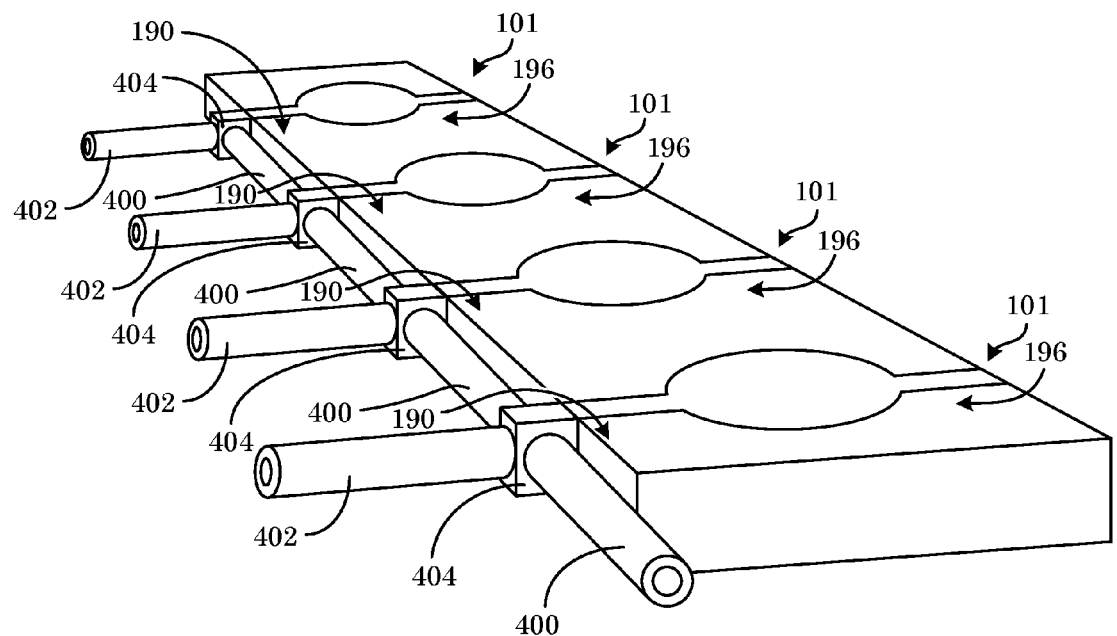
FIG. 29 shows an array of resonators.

According to an embodiment, acoustic article 100 includes a plurality of resonators 101 as shown in FIG. 29. Although four resonators 101 are shown in FIG. 29, a number of resonators 101 can be selected to provide independent evaluation of an effect of a plurality of samples delivered to individual resonators 101, wherein the samples can be identical or different among resonators 101. Here, an analyte, e.g., a biological sample, can be provided in flow tube 400 that is connected to inlet channel 190 of resonator 101 through valve 404. Optionally, secondary flow tube 402 can be connected to inlet channel 190 via valve 404. Secondary flow tube 402 can provide a same or different fluid to piezoelectric member 104 as that provided by flow tube 400. In this manner, a biological sample can be provided to the piezoelectric member 104 through flow tube 400, and an antimicrobial agent (e.g., an antibiotic) can be provided to piezoelectric member 104 through secondary flow tube 402. Moreover, in the plurality of secondary flow tube 402 shown in FIG. 29, individual secondary flow tubes 402 independently can provide a same or different fluid such as the antimicrobial agent to piezoelectric member 104. As a result, the biological sample disposed on each of piezoelectric member's 104 in the plurality of resonators 101 can be subjected to a plurality of different antimicrobial agents in parallel.

Electronic components can be included in acoustic article 100 to control fluid delivery or removal from piezoelectric member 104, control or detection of phase noise of piezoelectric 104, and the like. In an embodiment, with reference to FIG. 30, acoustic article 100 includes reference arm 218 in electrical communication with resonator 101 (e.g., electrodes 108, 110, 182, 180) through communication path (201, 203). Reference arm 218 can include active components or reactive components. Reference arm 218 arranged to be an active reference arm can include an amplifier. Reference arm 218 arranged to be a reactive reference arm can include an inductor, a capacitor in series with a 180° phase shifter, and the like.

Figure 30:
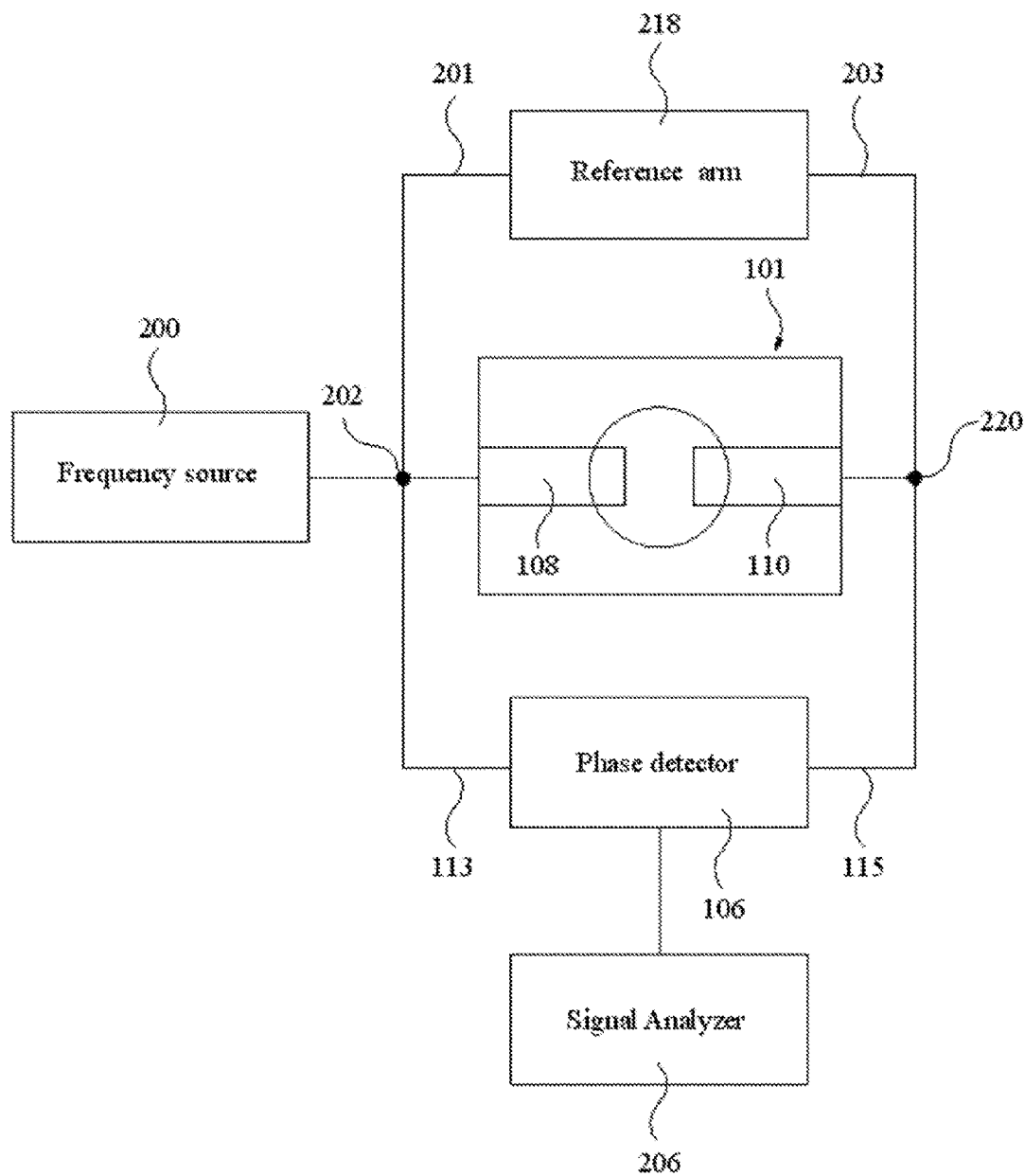
FIG. 30 shows a phase noise detector in combination with a passive bridge to detect phase noise from a resonator.

For active reference arm 218, with reference to FIG. 30, the loop formed by resonator 101, path 201, reference arm 218, and path 203 can form an oscillator that is locked to a resonant frequency of resonator 101. Here, frequency source 200 does not provide an excitation to resonator 101 or reference arm 218 and can be removed or can provide a high-stability reference signal to phase detector 106 through path 113.

For purely reactive reference arm 218, with reference to FIG. 30, high-stability frequency source 200 provides a continuous wave (CW) voltage excitation to electrode 108 of resonator 101 through splitter 202 and also to reference arm 218 through splitter 202 and path 201. Combiner 220 adds the voltages from electrode 110 and reference arm 218. Paths 113 and 115 communicate signals from splitter 202 and combiner 220 to phase detector 106.

Frequency source 200 provides a CW voltage with a frequency that can be selected to be close to a resonant frequency of piezoelectric member 104. The selected amplitude of frequency source 200 can be tenths of a volt to tens of volts. The output of frequency source 200 can have a phase noise level that is less than a phase noise level from biologically induced fluctuations of the excited resonance of piezoelectric member 104.

In an embodiment, the CW excitation voltage provides an RF electric field that is normal with respect to a surface (e.g., 158, 160) of piezoelectric member 104 that is exposed to the sample disposed thereon. In some embodiments, the CW excitation voltage provides an RF electric field that is in-plane with respect to a surface (e.g., 158, 160) of piezoelectric member 104 that is exposed to the sample disposed thereon, such that the excitation of piezoelectric member 104 is lateral-field excitation.

With reference to FIG. 30, phase noise detector 106 provides a voltage proportional to the difference in phase of the CW voltage from the frequency source 200 and the oscillating voltage that is communicated from the delay line 204 through path 115. Phase noise detector 106 can be a phase-sensitive electrical circuit with a voltage output that can be positive or negative and in the range of zero to several volts.

Phase noise detector 106 is in electrical communication with signal analyzer 206 that can be, e.g., a vector signal analyzer. Signal analyzer 206 provides a spectrum of the frequency components of the signal from the phase noise detector 106. This spectrum can be in the form of power spectral density. Signal analyzer 206 can be configured to span a sub-range of frequencies in the range of a hundredth of a Hertz (Hz) to a megahertz (MHz).

Figure 31:
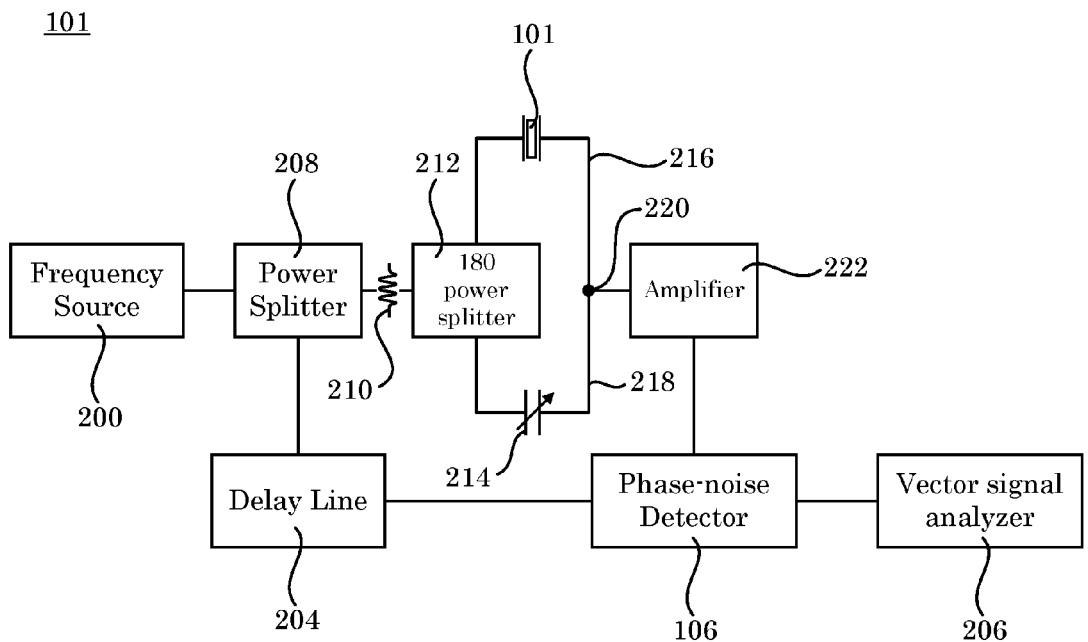
FIG. 31 shows a passive bridge circuit to detect phase noise from a resonator.

According to an embodiment, as shown in FIG. 31, a passive bridge circuit to measure phase noise of resonator 101 includes frequency source 200 to provide a high stability tunable frequency to power splitter 208. Power splitter 208 communicates a portion of the power to delay line 204 and a portion of the power to power adjuster 210 (e.g., a variable resistance resistor), which communicates the adjusted power to power splitter 212 of the passive bridge and provides some of the power to reference arm 218 that includes tunable capacitor 214 and provides some of the power to resonator arm 216 that includes resonator 101. Electrical signals from reference arm 218 and resonator arm 216 of the passive bridge or combined at combiner 220 and communicated to amplifier 222. Delay line 204 is in communication with phase noise detector 106 that receives the high stability tunable frequency from frequency source 200 subject to a selected time or phase delay by delay line 204. Phase noise detector 106 also receives a signal from amplifier 222 produced by the output of the bridge, which consists of the reference arm and resonator 101. Output from phase noise detector 106 is communicated to signal analyzer 206.

Resonator 101 includes piezoelectric member 104 that acoustically vibrates in response to being subjected by an excitation signal provided by electrodes (e.g., 108, 110). Piezoelectric member 104 can be a material that produces acoustic vibration, e.g., a quartz crystal. A physical cut of the quartz crystal provides selection over physical characteristics of the resonator such as acoustic vibrational frequency and direction of vibrational displacements. Exemplary quartz-crystal cuts that have resonant modes with displacements primarily in the plane of surfaces 158 and 160 of piezoelectric element 104 include AT, Y, and SC cuts, and the like.

Other exemplary materials for piezoelectric member 104 include single crystals with crystalline structures similar to langasite (langasite, langatate, $Ca_3TaGa_3Si_2O_{14}$, etc.), lithium niobate, and the like. Exemplary thin-film piezoelectric materials include aluminum nitride (AlN) and zinc oxide (ZnO).

Substrate 102 can be the same or different material from piezoelectric member 104. Exemplary materials for substrate 100 include quartz, silicon, silica, ceramics, and the like.

Electrodes (108, 110, 180, 182) are electrically conductive to provide the excitation signal to piezoelectric member 104 and to communicate the phase noise signal from piezoelectric member 104 to phase noise detector 106.

The sample is provided as a fluid disposed on piezoelectric member 104 and can include a variety of substances that can be a single component composition or a plural component composition. The sample can include biological particles with dimensions from sub-micron to hundreds of microns, and can be at a temperature between the freezing temperature and boiling temperature of the fluid.

In an embodiment, sample is a biological sample including microbes of one or more distinct species, strains, or phenotypes. The microbes can be innocuous, pathogenic, or beneficial to a biological or physical system. The microbes can be bacteria, archaea, or eukarya. In an embodiment, the microbe is pathogenic and has a motion on piezoelectric member 104. The motion may arise from any source indicative of microbial viability, including but not limited to cellular motility, movement of enzymatic complexes within the cell or on its surface, rearrangements of nucleic acids, or active modifications of cellular structure. In an embodiment, the motion is affected (e.g., increased or decreased) by a chemical, physical, or biological agent in the fluid.

The agent in the fluid that affects the motion of the analyte can be an antimicrobial agent that is an antibiotic, fungicide, biocide, or general modifier of solution chemistry such as the hydrogen ion (pH) or dissolved oxygen, and the like.

According to an embodiment, the phase noise signal of piezoelectric member 104, wherein a power spectral density of the phase noise signal decreases when the microbes are in a presence of an antimicrobial agent that is effective to decrease a motion of the microbes on the piezoelectric member. In this manner the phase noise signal can be used to analyze the effect of the antimicrobial agent on the microbes, wherein the decrease in motion of the microbes is due to decreased viability of the microbes.

With regard to the sample, particularly a biological sample that includes cells such as microbes, a chemical linker can be disposed on a surface of piezoelectric member 104 to adsorb the sample on piezoelectric member 104. It is contemplated that the chemical linker is exposed to the biological sample and can be selected and provided to mediate adsorption of the biological sample on piezoelectric member 104. Exemplary chemical linkers include poly-L-lysine, (3-aminopropyl)triethoxysilane, cell-specific antibodies, and the like. A positively charged group such as poly-L-lysine interacts with negatively charged cellular surfaces in the biological sample. Cell-specific antibodies interact with ligands on cell surfaces. The antibodies themselves can be covalently linked to thiol groups that form a self-assembled monolayer on, for example, a gold substrate.

Figure 32:
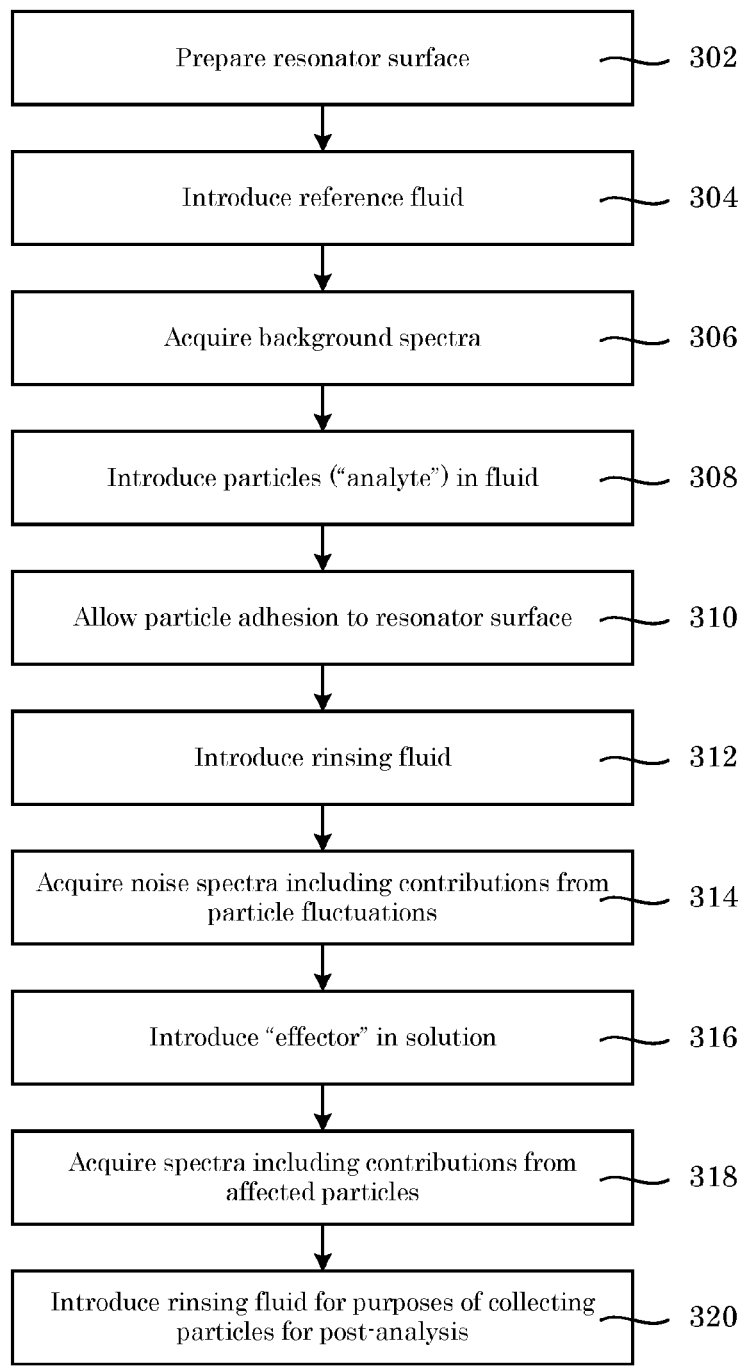
FIG. 32 shows a flow chart for a process for assaying a biolgial sample.

Acoustic article 101 can be made by providing substrate 102; providing piezoelectric member 104 disposed on substrate 102; disposing electrodes on piezoelectric member 104; electrically connecting the electrodes to phase noise detector 106. Substrate 102 can be made by a process of growing single crystals or a process of sintering ceramic particles. Piezoelectric member 104 can be disposed on substrate 102 by chemically etching a piezoelectric substrate to provide a monolithic inverted-mesa structure or by depositing piezoelectric material on a nonpiezoelectric substrate with a thin-film deposition process (e.g., sputtering or evaporation). Inlet channel 190 and outlet channel 196 can be disposed on or in substrate 102, e.g., by etching. Methods for fabricating composite embodiments of acoustic article 101 can include attaching piezoelectric member 104 to substrate 102 with an adhesive or a mechanical fastener The process and articles herein have numerous beneficial uses, including performing an assay on a biological sample containing microbes. In an embodiment, with reference to FIG. 32, a process for acquiring phase noise or frequency noise arising from motional fluctuations of an analyte (e.g., a plurality of cells such as microbes) disposed on piezoelectric member 104 includes providing acoustic article 100 that includes piezoelectric member 104 disposed on substrate 102; preparing a surface (e.g., 158 or 160) of piezoelectric member 104 to receive the analytes (step 302), wherein preparing the surface can include cleaning the surface or subjecting the surface to a chemical or biological, specific or non-specific adhesion promoter to promote adhesion of the analyte to piezoelectric member 104; introducing a reference sample (e.g., a fluid) to contact piezoelectric member 104, wherein the reference fluid includes a composition in an absence of the analyte (step 304); subjecting piezoelectric member 104 to the excitation signal; acoustically vibrating piezoelectric member 104 at a resonator frequency in response to receiving the excitation signal by piezoelectric member 104; acquiring reference phase signal (i.e., a background spectrum of phase noise) from piezoelectric member 104 in response to presence of the reference fluid in contact with piezoelectric member 104 (step 306); contacting piezoelectric member 104 with an analyte fluid (e.g., a biological sample) that include the analyte (step 308); adhering the analyte to piezoelectric member 104 in a presence or absence of a dynamic flow of analyte fluid (step 310); contacting piezoelectric member 104 with a rinse fluid to terminate disposition of the analyte on piezoelectric member 104 or to remove analyte that is not adhered to piezoelectric member 104 (step 312), wherein the rinse fluid includes a composition in an absence of the analyte; acquiring phase noise spectra from piezoelectric member 104, wherein the phase noise spectra includes a contribution from motional fluctuations of the analyte disposed on piezoelectric member 104 (step 314); contacting the analytes adsorbed on piezoelectric member 104 with an effector fluid including an effector (e.g., an antimicrobial agent such as an antibiotic in solution, a solution of different salinity or pH than the analyte fluid, and the like) (step 316); acquiring phase nose spectra from piezoelectric member 104, wherein the phase noise spectra includes a contribution from motional fluctuations of the analytes (step 318); contacting the analytes adsorbed on piezoelectric member 104 with a flushing fluid to remove the analytes from piezoelectric member 104 (step 320); collecting the analytes removed from piezoelectric member 104 by the flushing fluid; and (step 320); and performing analysis on the analytes removed from piezoelectric member 104.

Here, preparing the surface (e.g., 158 or 160) of piezoelectric member 104 can include cleaning the surface. Cleaning the surface includes solvent washes with light agitation (for example, methanol, acetone, isopropyl alcohol, and the like; light abrasion with a detergent (for example, sodium dodecyl sulfate and the like); and/or treatment by ultraviolet light and ozone in combination.

Preparing the surface (e.g., 158 or 160) of piezoelectric member 104 can include subjecting the surface to a chemical or biological, specific or nonspecific adhesion promoter. Subjecting the surface to the adhesion promoter involves liquid or vapor deposition of the adhesion promoter for a period of time ranging from 30 seconds to a number of days. Exemplary chemical adhesion promoters include charged molecules such as poly-L-lysine or (3-aminopropyl)triethoxysilane. Exemplary biological adhesion promoters include antibodies specific to cell types being assayed.

As used herein, the phrase "to promote adhesion" enhancement of the likelihood of attachment or strength of attachment of analyte to the surface of piezoelectric member 104. Specific adhesion promotion refers to antibodies. Nonspecific adhesion promotion refers to charged species.

Further, introducing the reference fluid to contact piezoelectric member 104 involves pumping the reference fluid at velocities less than one milliliter per minute through tubing connected to inlet and outlet ports of the module housing the crystal. Exemplary reference fluids include phosphate-buffered saline (a.k.a. PBS), or other common near-neutral pH buffers used for biological research. Reference fluids may also be comprised of common microbial growth media, such as Luria Broth or Tryptone Broth.

In the process, subjecting piezoelectric member 104 to the excitation signal involves passing a continuous-wave (CW) voltage from the excitation source 202 to the resonator 101 through path 113. The frequency of this excitation for a selected resonant mode of piezoelectric member 104 is set by optimizing the output signal from the resonator that is passed through path 115. The process of tuning the excitation frequency to the resonant frequency can include measurements of the RF amplitude from amplifier 222.

The acoustic vibration of the piezoelectric member 104 consists of standing waves with phase variation primarily through the thickness of the piezoelectric member 104 at the fundamental resonant frequency or one overtone resonant frequency of (i.e., fundamental or overtone thickness-shear resonances). Specifically, the frequency of vibration is approximately equal to an odd-integer multiple of an acoustic velocity in the direction normal to the piezoelectric surface divided by two times the thickness of the piezoelectric member 104. The selected acoustic velocity can be a shear-wave velocity, which provides advantages over longitudinal waves with respect to fluid damping of piezoelectric member 104.

Acquiring the background spectrum of phase noise from piezoelectric member 104 includes, first, adjusting the delay line 204 to approximately match the average phases of the signal from the resonator and the sinusoid from the frequency source. This adjustment involves zeroing a voltage displayed on phase noise detector 106 that is a measure of the average phase difference. After this adjustment, acquisition of a spectrum by signal analyzer 206 involves setting the frequency range, resolution bandwidth, and number of averages on this analyzer. Initiation of acquisition of an averaged spectrum can be performed by pressing a button on analyzer 206 or by computer control of this instrument.

Contacting piezoelectric member 104 with the analyte fluid includes administering analyte fluid to the face of the piezoelectric member, either by pumped fluid flow, pipetting, immersion, or the like. The analyte fluid can include water with or without nutrients or other chemicals that promote or inhibit growth and/or motion of the analyte. The analytes can include biological cells or non-biological colloidal particles.

Adhering analytes to piezoelectric member 104 includes allowing time without flow, and before administering rinse fluid, to enable analytes to settle on the surface. Adhering analytes to piezoelectric member 104 can also include the removal by flow of fluid from the surface, thereby employing surface tension of the small amount of remaining fluid to promote adhesion.

Contacting piezoelectric member 104 with the rinse fluid terminates disposition of analytes on piezoelectric member 104 or removes analytes that are not adhered to piezoelectric member 104. The rinse fluid can include phosphate-buffered saline (PBS), other buffers, or growth medium such as Luria Broth (LB), or other solutions that maintain the viability of the analytes.

Acquiring phase noise spectra from piezoelectric member 104, includes measuring and recording power spectral densities over a selected range of noise frequencies. The phase noise spectra include the contribution from motional fluctuations of analytes disposed on piezoelectric member 104. Here, motional fluctuations of the analytes can be swimming (motility constrained by adhesion to the surface of piezoelectric member 104), motion of the surfaces of the analyte particles, or motion arising from external forces, such as Brownian or thermal motion arising from the fluid.

The analytes adsorbed on piezoelectric member 104 are contacted with the effector fluid containing an effector such as an antibiotic, fungicide, biocide, or chemical modifier such as the hydrogen ion; or the effector fluid can purposefully omit a chemical species previously included in the analyte fluid, such as dissolved oxygen. The effector fluid can include the effector, growth stimulants (such as yeast extract, peptone, tryptone, and the like), salts and ionic species ($NaCl$, $K^+$, $Mg^{2+}$, $Ca^{2+}$, and the like) or a combination thereof. The effector fluid can be a defined minimal medium specific to the sample (e.g., microbe) being tested Additionally, the process includes contacting the analytes adsorbed on piezoelectric member 104 with the flushing fluid to remove the analytes from piezoelectric member 104. The flushing fluid disrupts adhesion among the analytes and the surface of piezoelectric member 104. The flushing fluid can include phosphate-buffered saline (PBS), other buffers, or growth medium such as Luria Broth (LB), or other solutions that maintain the viability of the analytes.

In collecting the analytes removed from piezoelectric member 104 by the flushing fluid, analytes can be collected by collection of the effluent flushing liquid, which can be flushed at higher flow rates than those used to administer analytes to the piezoelectric member. Additionally, the piezoelectric member may be removed from the module without disturbing analytes on the surface, and then lightly agitated in a new volume of flushing fluid. After some time, this flushing fluid can be collected by pipette for analysis.

After collecting the analytes, analysis is performed on the analytes. The analysis can include any number of traditional biological or non-biological assays, but specifically the serial dilution and plating of microbial analytes onto growthpromoting agar for the purposes of counting colony-forming units (CFUs) among the analytes.

It is contemplated that acoustic article 100 provides assessment of samples in a clinical setting. In an embodiment, a process for assaying a biological sample includes receiving a reference sample by acoustic article 100 that includes: resonator 101 (e.g., including substrate 102; piezoelectric member 104 disposed on substrate 102; and phase noise detector 106 in electrical communication with piezoelectric member 104); disposing the reference sample on piezoelectric member 104; producing a reference phase noise signal in response to piezoelectric member 104 being in contact with the reference sample; detecting the first phase noise signal by phase noise detector 106; disposing a biological sample on piezoelectric member 104, the biological sample including a microbe having a motional fluctuation on piezoelectric member 104; producing a first biological phase noise signal in response to piezoelectric member 104 being in contact with the biological sample; detecting the first biological phase noise signal by phase noise detector 106; contacting the biological sample disposed on piezoelectric member 104 with an effector (e.g., an antimicrobial agent); producing a second biological phase noise signal in response to piezoelectric member 104 being in contact with the biological sample; detecting the second biological phase noise signal by phase noise detector 106; and analyzing the first biological phase noise signal, the second biological phase noise signal, and the reference phase noise signal to assay the biological sample. Here, analyzing the first biological phase noise signal, the second biological phase noise signal, and the reference phase noise signal includes subtraction of the reference phase noise signal from both the first and second biological phase noise signals, and comparison of the first and second phase noise signals after reference subtraction to determine the direction and magnitude of signal change in response to the effector. Assaying the biological sample can include comparing a change in a first signal from a first acoustic resonator that includes a first resonator 104 in a presence of a sample (e.g., a biological sample that includes, e.g., microbes) in a presence of an effector with a change in signal from a second acoustic article that includes a second resonator. Here, the second resonator produces the second signal in response to the disposal of a sample that is compositionally identical to that disposed on the first resonator but in an absence of the effector.

The process for assaying the biological sample also can include determining a reference power spectral density from the reference phase noise signal; determining a first power spectral density from the first biological phase noise signal; and determining a second power spectral density from the second biological phase noise signal. In an embodiment, the process includes determining that the effector decreases the activity, e.g., motional fluctuation, of the microbes if the second power spectral density is less than the first power spectral density in view of the reference power spectral density In some embodiments, the process includes determining that the effector does not increase the activity, e.g., the motional fluctuation of the microbe if the second power spectral density is greater than the first power spectral density in view of the reference power spectral density.

The sample (e.g., the biological sample) disposed on piezoelectric member 104 can include microbes and a growth medium to provide for growth of the microbes (e.g., division and the like). It is contemplated that certain effectors (e.g., particular antimicrobials) can be effective or ineffective against the microbes, but the growth medium of the sample can still stimulate growth of the microbes in a presence of the effector. As a result, phase noise from piezoelectric member 104 of acoustic article 100 increases due to microbes in presence of the growth medium and the effector that is ineffective against the microbes.

In an embodiment, a first sample and an effector that includes an antibiotic is disposed on a first acoustic article (also referred to a test acoustic article), wherein the sample includes a plurality of different microbial species, and wherein a first species of the microbes responds to the antibiotic of the effector, while a second species of microbes in the sample grow and divide due to the effector being ineffective against the second species. The first acoustic article includes a first piezoelectric member that produces a first phase noise signal (also referred to as a test phase noise signal) in response to the first sample. Here, the antibiotic is effective against the first species in the first sample, but the first phase noise continues to increase rather than decrease. Additionally, a second acoustic article (also referred to as a control acoustic article) is provided to provide a second phase noise signal (also referred to as control phase noise signal) from its piezoelectric member in response to presence of a second sample (also referred to as a control sample), wherein second sample includes all components of the first sample in an absence of the effector.

The first phase noise signal from the piezoelectric member of the first acoustic article is compared against the second phase noise signal from the second acoustic article. Here, if the first phase noise decreases, and the second phase noise does not decrease, the antimicrobial of the effector is determined to decrease an activity (e.g., motional fluctuations) of the microbes. Alternatively, if the first phase noise does not change from the first acoustic article in response the microbes in presence of the effector, and the second phase noise increases from the second acoustic article that performs as the control, the antimicrobial of the effect is determined to decrease the activity (e.g., fluctuations) of the microbes. Further alternatively, if the first phase noise from the first acoustic article increases due to the microbes in presence of the effector, and the second phase noise from the second acoustic article (control) increases more that the first phase noise, the antimicrobial of the effector is determined to decrease the activity (e.g., fluctuations) of a subpopulation of the microbes.

In contemplation of these various results for a change of the first phase noise from the first acoustic article, compensation for time-dependent changes in power spectral densities of the first phase noise signal arising from changes in cell growth and division of components in the first sample includes normalization of power spectral densities of the first phase noise signal with respect to the time-dependent power spectral densities produced from the second phase noise signal provided by the second acoustic article (performing as the control acoustic article) with the second sample and data acquisition process that are substantially similar to that for the first acoustic article, except for an absence of exposure to the effector for the second acoustic article.

Advantageously, embodiments include sensing of mechanical fluctuations of pathogenic bacteria and time-dependent changes in these fluctuations that occur upon exposure of the bacteria to antibiotics. Embodiments provide characterization of an effectiveness of an antibiotic in treatment of an infection in a more rapid time than certain conventional culturing techniques and more directly than certain genomic-based techniques.

In an embodiment, a method for characterizing a response of bacteria to an antibiotic includes introducing a cell-free reference fluid; acquiring an initial baseline noise with the resonator in a cell-free solution; introducing a fluid containing bacteria from a clinical sample through fluid channels to the surface of the resonator; waiting a period in which cells adhere to the surface of the resonator, with or without a previously deposited layer that facilitates specific or non-specific adhesion; acquiring noise spectra with the cells on the resonator; introducing an antibiotic, a cocktail of antibiotics, or biocide in solution; monitoring of time-dependent changes in noise spectra as the bacteria are exposed to the antibiotic; recovering the affected bacteria for subsequent testing; or a combination thereof.

A reduction in power spectral density of the noise can reflect changes in associated microbial fluctuations, enabling characterization of antibiotic efficacy. Acoustic article 100 can include a multiplexed array of inverted-mesa resonators etched in a single wafer such that a library of candidate antibiotics or biocides could be simultaneously tested.

Assaying samples can include providing acoustic article 100 that has multiplexed arrays of resonators 101 for combinatorial testing and developing new antibiotics, fungicidal drugs, or biocidal agents for nonmedical applications (e.g., biofouling and corrosion). Effects of environmental contaminants (e.g., fracking fluids and emerging contaminants) on microbes can be screened. Additionally, acoustic article 100 can characterize dynamics of non-biological self-propelled particles (e.g., colloidal motors) in various chemical environments.

The articles and processes herein are illustrated further by the following Examples, which are non-limiting.

EXAMPLES

Example 1

Exposure of a Biological Sample of *E. Coli* to Ampicillin

An acoustic article was prepared to detect microbial viability through measurements of phase noise of a resonator on which microbes were adhered. An acoustic article was prepared by combining a piezoelectric resonator (commercially available from Biolin Scientific, model Q-Sense) and custom fabricated components that interfaced to the piezoelectric resonator. The piezoelectric resonator included an electrical contact to a piezoelectric crystal. The piezoelectric crystal had a resonator frequency of 5 MHz and was made of AT-cut quartz, and gold electrodes were disposed on its two flat surfaces, such that voltages applied to the electrodes provided electric fields through the thickness of the crystal and induced shear displacements parallel to these surfaces. One side of the piezoelectric crystal faced a fluid chamber and was coated with a thin layer of poly-L-lysine (PLL) to promote adhesion of microbes to the surface. The piezoelectric resonator was disposed on an aluminum platform that incorporated electrical lines to the resonator, and the platform was placed on a thermally controlled platform held at a constant temperature of approximately 37° C. Phosphate-buffered saline (PBS) was introduced to the fluid chamber, and electronics configured according to FIG. 30 and FIG. 31 were used to determine the resonant frequency of the resonator by varying the output frequency from frequency source 200 while monitoring the amplitude of the RF output from amplifier 222. The output frequency of the CW voltage from the frequency source was then set to this measured resonant frequency. Subsequently, averaged power spectral densities of phase noise from the resonator were determined from the measured time-varying voltage from phase-noise detector 106 passed to vector signal analyzer 206, through the use of a calibration of phase-noise detector 106. Following acquisition of this background spectrum, *Escherichia coli* (*E. coli*) cells were suspended in PBS and flowed through the fluid chamber over the crystal for five minutes. The chamber was then drained of fluid and refilled with Luria-Bertani (LB) broth to provide nutrients for bacterial growth. *E. coli* adhered to the crystal surface during this sequence, and unattached cells were washed away.

Figure 33:
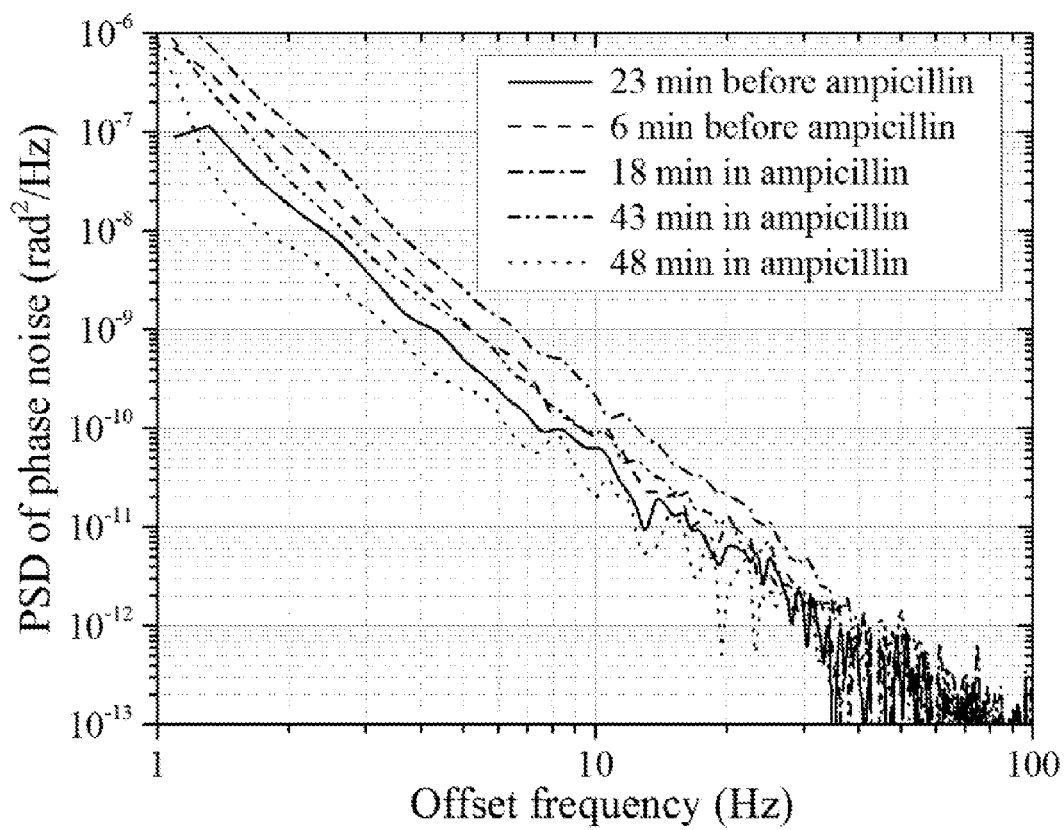
FIG. 33 shows a graph of power spectral density of phase noise versus offset frequency.

Power spectral densities (PSDs) were repeatedly acquired over a period beginning 30 minutes before ampicillin in LB was introduced to the crystal and ending 68 minutes after this introduction of ampicillin. Before the acquisition of each averaged spectrum, the output of frequency source 200 was retuned to the current frequency of the resonator while monitoring the output of amplifier 222. FIG. 33 shows examples of measured power spectral densities of phase noise over a range of 1 Hz to 100 Hz at several times in the experiment, with the zero for time defined to be the time of introduction of ampicillin. The background PSD in PBS has been subtracted from these spectra.

Figure 34:
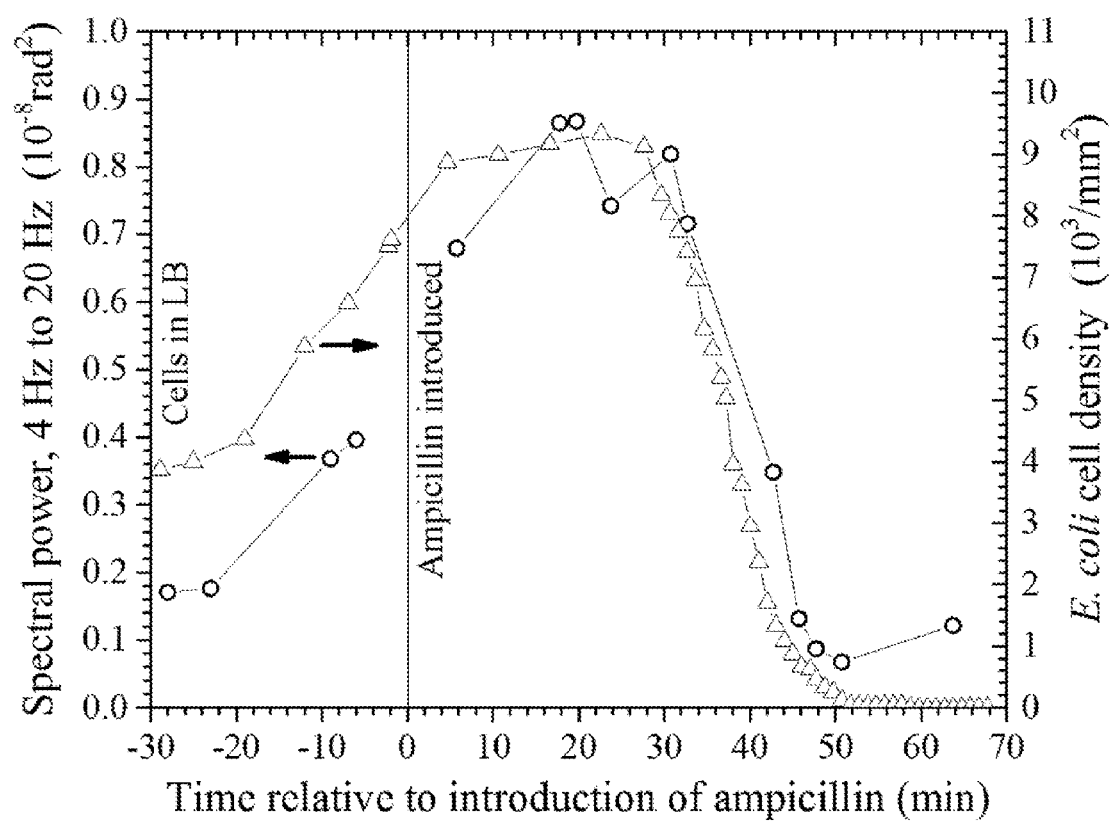
FIG. 34 shows a graph of spectral power and cell density versus time.

To provide a scalar quantity reflective of the measured PSDs, the spectra in FIG. 33 and similar spectra at other times during the experiment were integrated over the frequency range from 3 Hz to 20 Hz. This quantity, which is the total spectral power over this frequency range, is plotted in FIG. 34 as a function of time. These data show that the spectral power of phase noise increased with time before introduction of ampicillin, essentially leveled off soon after introduction of ampicillin, and began dropping towards the level of the background approximately 30 minutes after introduction of ampicillin. Simultaneous optical microscope images showed the cell density increasing through cell division during the period when the spectral power increased before introduction of ampicillin. The cell density dropped as a result of lysing and disintegration of cells during the period beginning 30 min after the introduction of ampicillin.

Simultaneous control measurements of PSDs were also acquired on a second piezoelectric crystal with the same sequence of introduction of fluids, except that the effector fluid contained no ampicillin. With this control crystal, PSDs increased continuously during the entire experiment. The general form of variation of PSDs and cell densities with time described here for crystals exposed and not exposed to ampicillin was observed in other similar experiments on *E. coli*

To confirm the action of the antibiotic on *E. coli* viability, cells were collected from the surface of the crystal and plated after serial dilution onto LB-agar plates for enumeration of colony-forming units (CFUs). After growth for at least 24 hours, the plate counts confirmed that exposure to ampicillin during the course of the experiment resulted in a several log decrease in the number of CFUs relative to a parallel sample not exposed to ampicillin.

Example 2

Exposure of a Biological Sample of *E. Coli* to Polymyxin B

The acoustic article, electronic circuitry, data acquisition procedures, and fluid-analyte processing steps described in Example 1 were used to probe the effect of an antibiotic, polymyxin B, on phase noise generated by *E. coli* Here, two identical resonators ("Crystal A" and "Crystal B") were used in which Crystal B was not exposed to polymyxin B until more than 40 minutes after introduction of polymyxin B to Crystal A.

Figure 35:
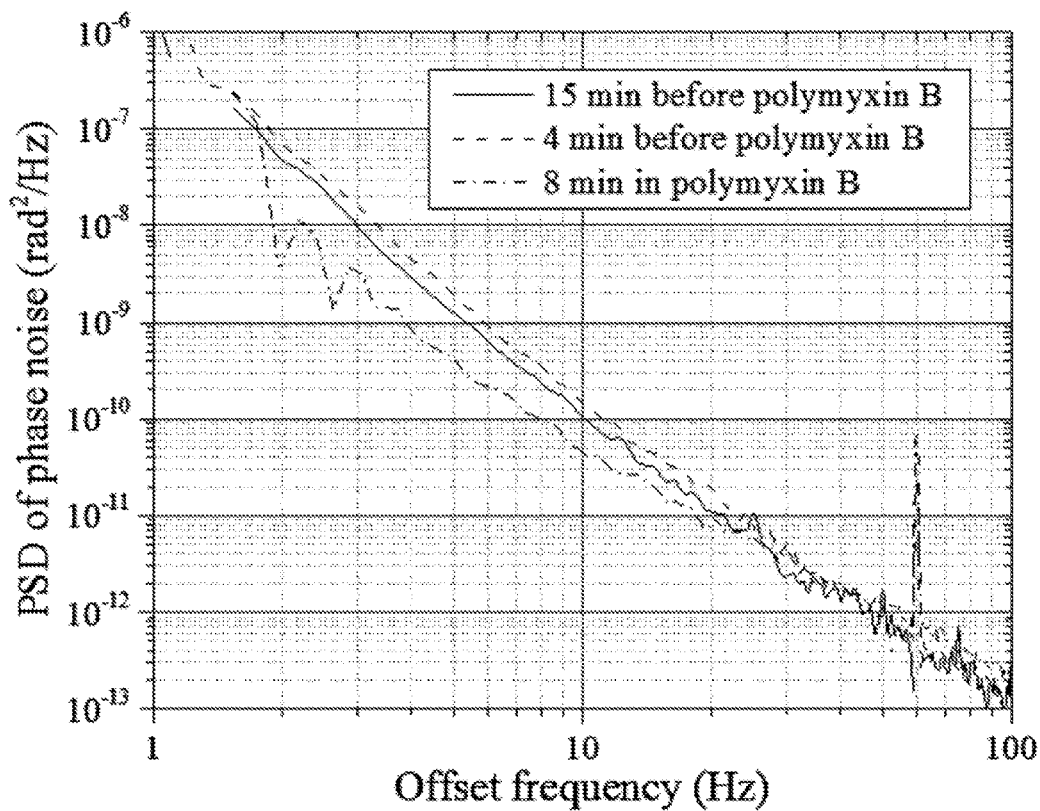
FIG. 35 shows a graph of power spectral density of phase noise versus offset frequency.
Figure 36:
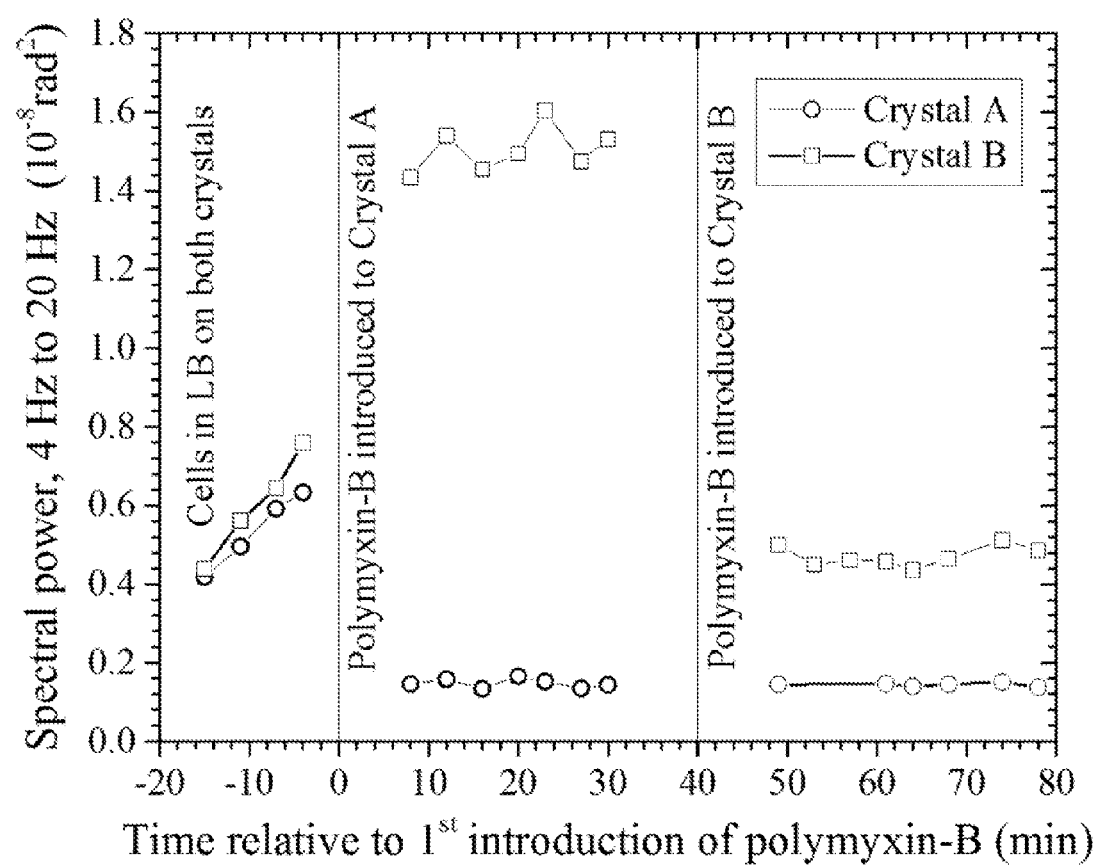
FIG. 36 shows a graph of spectral power versus time.

Measurements of PSDs of the first resonator (Crystal A) before and after exposure of *E. coli* to polymyxin B are shown in FIG. 35. FIG. 36 shows the corresponding spectral power from 4 Hz to 20 Hz for these spectra and other spectra over the period from 20 min before to 80 min after polymyxin B exposure. Data from second resonator Crystal B with *E. coli* not exposed to polymyxin B during 0-40 minutes are shown in FIG. 36 and labelled as "Crystal B," wherein data labelled as "Crystal A" are data taken in presence of polymyxin B during 0-40 minutes and later. As with ampicillin, PSDs of the acoustic resonators dropped dramatically when the antibiotic was introduced. Unlike ampicillin, polymyxin B does not induce a disintegration of *E. coli* cells.

Figure 37:
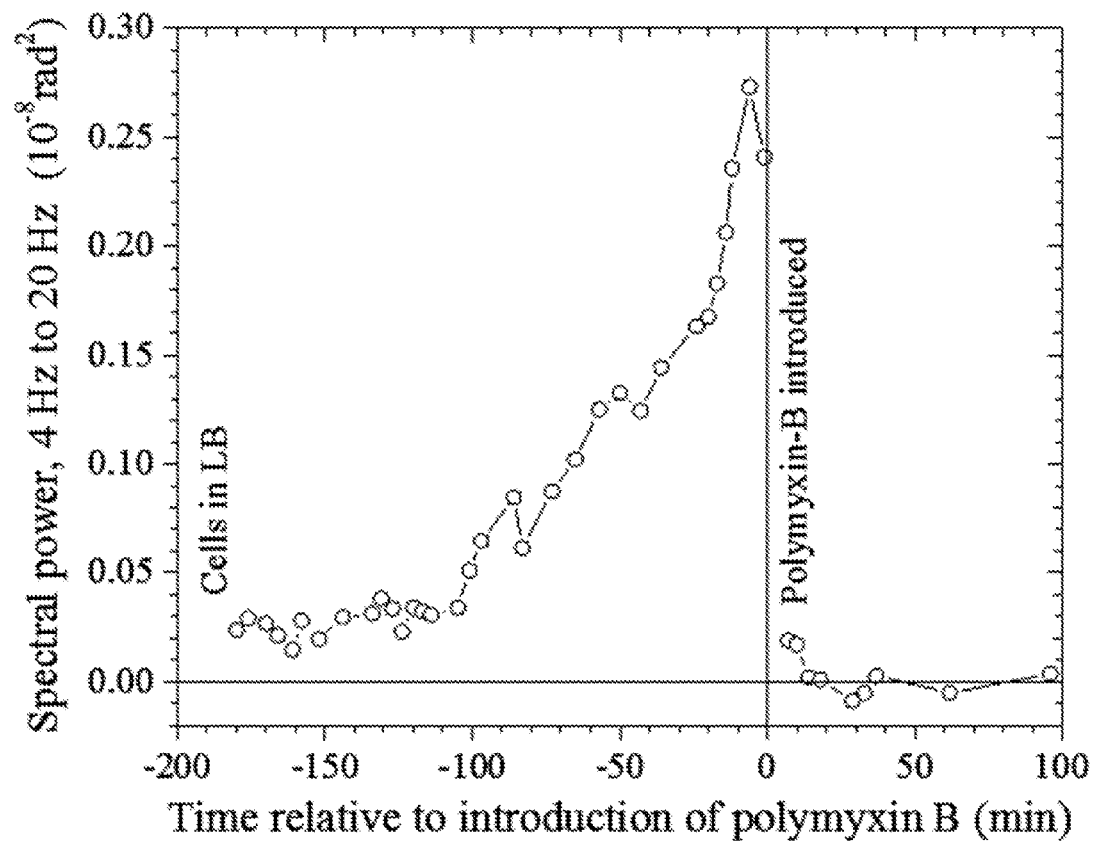
FIG. 37 shows a graph of spectral power versus time.

To confirm the action of the antibiotic on *E. coli* viability, cells were collected from the surface of the resonators (Crystal A and Crystal B) and plated after serial dilution onto LB-agar plates for enumeration of colony-forming units (CFUs). After growth for at least 24 hours, the plate counts confirmed that exposure to polymyxin B during the course of the experiment resulted in a greater than several log decrease in the number of CFUs relative to a parallel sample not exposed to polymyxin B. In fact, no CFUs were recovered from the polymyxin B-treated resonators. Data for this examination is shown in FIG. 37.

Preliminary experiments with both ampicillin and polymyxin B indicate that the resonator method is sufficient to detect antimicrobial action against live *E. coli* cells within a one-hour time frame.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An acoustic article for assaying a biological sample, the article comprising:
   a resonator comprising:
      a substrate comprising an inverted mesa structure;
      a piezoelectric member disposed on the substrate to receive the biological sample and to produce a phase noise signal, the phase noise signal indicating activity of the biological sample; and
   a phase noise detector in electrical communication with the piezoelectric member to receive the phase noise signal from the piezoelectric member and to produce a phase noise spectrum in response to receiving the phase noise signal from the piezoelectric member.

2. The acoustic article of claim 1, further comprising:
   a plurality of electrodes disposed on the piezoelectric member to provide excitation of vibration of the piezoelectric member.

3. The acoustic article of claim 1, further comprising:
   a first fluid channel disposed on the substrate to communicate a fluid comprising the biological sample to the piezoelectric member.

4. The acoustic article of claim 3, further comprising:
   a second fluid channel disposed on the substrate to communicate the fluid from the piezoelectric member.

5. The acoustic article of claim 1, further comprising:
   an excitation source to provide an excitation signal to the piezoelectric member.

6. The acoustic article of claim 5, wherein the excitation signal comprises a continuous-wave (CW) voltage that provides an RF electric field that is normal or parallel a surface of piezoelectric member.

7. The acoustic article of claim 5, wherein the excitation signal is provided by a high-stability frequency source through a passive electrical bridge, with the resonator in a first arm of the bridge and a balancing capacitor in a second arm of the bridge
   such that an output of the passive electrical bridge is dominated by a resonance of the acoustic article.

8. The acoustic article of claim 1, further comprising the biological sample, wherein the biological sample comprises a plurality of microbial cells.

9. The acoustic article of claim 8, wherein the microbial cells comprises bacteria, archaea, fungi, a eukaryotic microbe, or a combination thereof.

10. The acoustic article of claim 8, wherein a power spectral density of the phase noise signal decreases when the microbe is in a presence of an antimicrobial agent that is effective to decrease activity of the microbe on the piezoelectric member.

11. The acoustic article of claim 10, wherein the antimicrobial agent comprises an antibiotic, fungicide, biocide, or a combination thereof.

12. The acoustic article of claim 1, wherein the decrease in motion of the microbe is due to decreased activity of the microbe.

13. The acoustic article of claim 1, wherein the substrate comprises an inverted mesa structure.

14. The acoustic article of claim 13, wherein the piezoelectric member comprises a quartz crystal.

15. The acoustic article of claim 13, further comprising a chemical linker disposed on a surface of the piezoelectric member, the chemical linker being exposed to the biological sample and provided to mediate adsorption of the biological sample on the piezoelectric member.

16. An acoustic article for assaying a biological sample, the article comprising:
   a resonator comprising:
      a substrate; and
      a piezoelectric member disposed on the substrate to receive the biological sample and to produce a phase noise signal, the phase noise signal indicating activity of the biological sample, and the substrate and piezoelectric member arranged to form a solidly mounted bulk resonator; and
   a phase noise detector in electrical communication with the piezoelectric member to receive the phase noise signal from the piezoelectric member and to produce a phase noise spectrum in response to receiving the phase noise signal from the piezoelectric member.

* * * * *